United States Patent
Lim et al.

(10) Patent No.: US 11,059,870 B2
(45) Date of Patent: Jul. 13, 2021

(54) POLYPEPTIDES WITH PHASE TRANSITION, TRIBLOCK POLYPEPTIDES OF THE POLYPEPTIDE-CALMODULIN-POLYPEPTIDE WITH MULTI-STIMULI RESPONSIVENESS, HYDROGEL OF THE TRIBLOCK POLYPEPTIDES, AND ITS USES

(71) Applicant: INDUSTRY-UNIVERSITY COOPERATION FOUNDATION HANYANG UNIVERSITY ERICA CAMPUS, Ansan-si (KR)

(72) Inventors: Dong Woo Lim, Ansan-si (KR); Jae Sang Lee, Ansan-si (KR); Min Jung Kang, Bucheon-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 318 days.

(21) Appl. No.: 15/744,210

(22) PCT Filed: Apr. 7, 2016

(86) PCT No.: PCT/KR2016/003658
§ 371 (c)(1),
(2) Date: Jan. 12, 2018

(87) PCT Pub. No.: WO2017/159915
PCT Pub. Date: Sep. 21, 2017

(65) Prior Publication Data
US 2020/0270317 A1    Aug. 27, 2020

(30) Foreign Application Priority Data
Mar. 14, 2016   (KR) .................. 10-2016-0030238

(51) Int. Cl.
| | | |
|---|---|---|
| *C07K 14/47* | (2006.01) | |
| *A61L 27/22* | (2006.01) | |
| *A61L 27/52* | (2006.01) | |
| *C07K 7/06* | (2006.01) | |
| *C07K 14/78* | (2006.01) | |

(52) U.S. Cl.
CPC .............. *C07K 14/47* (2013.01); *A61L 27/22* (2013.01); *A61L 27/52* (2013.01); *C07K 7/06* (2013.01); *C07K 14/78* (2013.01)

(58) Field of Classification Search
CPC .... C07K 14/78; C07K 2319/00; C07K 19/00; C07K 2319/735; C07K 14/4728
See application file for complete search history.

(56) References Cited

U.S. PATENT DOCUMENTS

2004/0171545 A1*  9/2004  Chaikof .................. A61L 31/16
                                                                 514/9.4
2011/0039776 A1    2/2011  Chilkoti

FOREIGN PATENT DOCUMENTS

| JP | 1209167 A1 * | 5/2002 | .......... C07K 14/435 |
|---|---|---|---|
| JP | 2010-502734 A | 1/2010 | |
| JP | 2012-232961 A | 11/2012 | |
| WO | WO 2015/051001 A2 | 4/2015 | |

OTHER PUBLICATIONS

Banta et al. Protein Engineering in the Development of Functional Hydrogels. Annu. Rev. Biomed. Eng. 2010. 12:167-86. (Year: 2010).*
Kowalczyk et al., "Elastin-like Polypeptides as a Promising Family of Genetically-engineered Protein Based Polymers", World Journal of Microbiology and Biotechnology, 2014, pp. 2141-2152, vol. 30.
Im, Dong Woo et al., "Injectable Polypeptide Hydrogels with Stimuli-responsiveness for Biomedical Applications", The Polymer Society of Korea, Korea-Japan Joint Symposium: Sustainable Plastics and Biopolymers, Apr. 2015, vol. 40, No. 1.
Hwang, Eun Young et al., "Surface Enhanced Roman Scattering-based Biosensing and Bioimaging of Metallic Nanoparticle Cluster-embedded Hierarchical Nanoarchitectures", The Polymer Society of Korea, Soft Sensor and Actuator, Oct. 2015, vol. 40, No. 2.
Im, Dong Woo et al., "Improved Non-chromatographic Purification of a Recombinant Protein by Cationic Elastin-like Polypeptides", Bioacromolecules, 2007, pp. 1417-1424, vol. 8.
Dan E. Meyer et al., "Protein Purification by Inverse Transition Cycling", Protein-Protein Interactions: A Molecular Cloning Manual, 2002, pp. 329-343, Chapter 18.
Dan W. Urry et al., "Temperature of Polypeptide Inverse Temperature Transition Depends on Mean Residue Hydrophobicity", J. Am. Chem. Soc., 1991, pp. 4346-4348, vol. 113.

* cited by examiner

*Primary Examiner* — Soren Harward
*Assistant Examiner* — Jia-Hai Lee
(74) *Attorney, Agent, or Firm* — Rabin & Berdo, P.C.

(57) ABSTRACT

Disclosed is a polypeptide having a phase transition behavior, wherein the polypeptide consists of a Val-Pro-Gly-Xaa-Gly (SEQ ID NO: 1) pentapeptide repeat or a Val-Pro-Ala-Xaa-Gly (SEQ ID NO: 2) pentapeptide repeat, and the polypeptide includes a [Val-Pro-Gly-Xaa-Gly (SEQ ID NO: 1)]n or a [Val-Pro-Ala-Xaa-Gly (SEQ ID NO: 1)]n pentapeptide repeat. In addition, the present invention provides a multi-stimuli polypeptide composed of polypeptide-calmodulin-polypeptide having a phase transition behavior and a hydrogel prepared using the same. A dynamic protein hydrogel according to the present invention may be used as a drug carrier, as a scaffold for tissue engineering or as a kit for tissue or organ regeneration.

11 Claims, 10 Drawing Sheets
Specification includes a Sequence Listing.

POLYPEPTIDES WITH PHASE TRANSITION, TRIBLOCK POLYPEPTIDES OF THE POLYPEPTIDE-CALMODULIN-POLYPEPTIDE WITH MULTI-STIMULI RESPONSIVENESS, HYDROGEL OF THE TRIBLOCK POLYPEPTIDES, AND ITS USES

CROSS-REFERENCE TO RELATED APPLICATION

This application claims priority to and the benefit of Korean Patent Application No. 2016-0030238, filed on Mar. 14, 2016, the disclosure of which is incorporated herein by reference in its entirety.

BACKGROUND

1. Field of the Invention

The present invention relates to a novel polypeptide having a phase transition behavior, a triblock polypeptide composed of the polypeptides and calmodulin (i.e., polypeptide-calmodulin-polypeptide) and having multi-stimuli responsiveness, and a hydrogel prepared using the triblock polypeptide. More particularly, the present invention relates to a novel thermally responsive elastin-based polypeptide (EBP), and a newly prepared triblock polypeptide based thereon. In addition, since the hydrogel of the present invention has dynamic properties causing a three-dimensional structural change, the dynamic hydrogel may be used in drug delivery systems, tissue engineering and regenerative medicine.

2. Description of Related Art

Stimuli-responsive protein-based biomaterials which exhibit a three-dimensional hydrogel network induced by sol-gel transition have been of great interest for a variety of biomedical applications because the biomaterials have unique characteristics including stimuli-triggered self-assembly, specific biological functions as well as controllable mechanical properties when hydrogelation occurs. In particular, when conformational changes in the biomaterials occur in response to environmental conditions such as temperature, pH, ionic strength and a ligand, protein hydrogels may undergo three dimensional changes. In this case, the protein hydrogels are called "dynamic hydrogels". Recently, genetically engineered protein-based materials have been developed as advanced biomaterials for drug delivery, tissue engineering and regenerative medicine applications because the materials have unique amino acid sequences derived from the original proteins of living organisms, monodisperse molecular weights designed at the gene level, excellent biocompatibility with low cytotoxicity, and adjustable biodegradability. Accordingly, a series of elastin, collagen, silk, resilin, calmodulin, metalloproteins, block polypeptides thereof and fusion proteins with biologically active moieties, to be used in preparation of various protein hydrogels for biomedical applications, have been reported.

The elastin-based polypeptides (EBPs) with a repeat unit of a pentapeptide, Val-Pro-(Gly or Ala)-$X_{aa}$-Gly (SEQ ID NO: 43), where $X_{aa}$ may be any amino acid other than Pro, have been studied because of the controllable environmental responsiveness thereof.

In general, there is a difficulty in applying chemically cross-linked EBP hydrogels to in vivo injectable systems due to cytotoxicity of reaction byproducts and reaction dynamics.

Therefore, the present inventors have continued to study elastin-based proteins that are formed by physical and chemical crosslinking at the same time and have dynamic properties. As a result, the present inventors have developed a novel elastin-based polypeptide, and based on the same, have completed preparation of a multi-stimuli responsive protein-based hydrogel suitable for biomaterial injection.

SUMMARY OF THE INVENTION

Therefore, the present invention has been made in view of the above problems, and it is an objective of the present invention to provide a novel polypeptide having a phase transition behavior.

It is another objective of the present invention to provide a novel triblock polypeptide including the polypeptide block.

It is still another objective of the present invention to provide a dynamic protein hydrogel prepared using the triblock polypeptide.

It is yet another objective of the present invention to provide a composition for drug delivery including the hydrogel.

It is yet another objective of the present invention to provide a scaffold for tissue engineering including the hydrogel.

It is yet another objective of the present invention to provide a kit for tissue or organ regeneration including the hydrogel.

In accordance with the present invention, the above and other objectives can be accomplished by the provision of a polypeptide below:

the polypeptide having a phase transition behavior, wherein the polypeptide consists of a Val-Pro-Gly-Xaa-Gly (SEQ ID NO:1) pentapeptide repeat or a Val-Pro-Ala-Xaa-Gly (SEQ ID NO:2) pentapeptide repeat, and wherein the polypeptide consists of an amino acid sequence represented by Formula 1 or 2 below and:

```
Formula 1
[Val-Pro-Gly-Xaa-Gly (SEQ ID NO: 1)]n;
or

Formula 2
[Val-Pro-Ala-Xaa-Gly (SEQ ID NO: 2)]n,
``` wherein n is an integer of 2 or more, and is the number of repeats of the pentapeptide; and Xaa is an amino acid other than proline, and is selected from any natural or artificial amino acid when the pentapeptide VPGXG (SEQ ID NO: 1) or VPAXG (SEQ ID NO: 2) is repeated.

The term "amino acid" used in the present invention refers to a natural or artificial amino acid, preferably a natural amino acid. For example, the amino acid includes glycine, alanine, serine, valine, leucine, isoleucine, methionine, glutamine, asparagine, cysteine, histidine, phenylalanine, arginine, tyrosine, tryptophan and the like.

As used herein, abbreviations such as Gly (G) and Ala (A) are amino acid abbreviations. Gly is an abbreviation for glycine, and Ala is an abbreviation for alanine. In addition, glycine is represented by G and alanine by A. The abbreviations are widely used in the art.

The term "polypeptide" used herein refers to any polymer chain composed of amino acids. The terms "peptide" and "protein" may be used interchangeably with the term polypeptide, and also refer to a polymer chain composed of amino acids. The term "polypeptide" includes natural or synthetic proteins, protein fragments and polypeptide analogs having protein sequences. A polypeptide may be a monomer or polymer.

The term "phase transition" refers to a change in the state of a material, such as when water turns into water vapor or ice turns into water.

The polypeptide according to the present invention is basically a stimuli-responsive elastin-based polypeptide (EBP). The "elastin-based polypeptide" is also called "elastin-like polypeptide (ELP)", and is a term widely used in the technical field of the present invention.

In the present specification, X (or $X_{aa}$) is referred to as "guest residue". Various types of EBPs according to the present invention may be prepared by variously introducing $X_{aa}$.

EBPs undergo a reversible phase transition at a lower critical solution temperature (LCST), also referred to as a transition temperature ($T_t$). EBPs are highly water-soluble below $T_t$, but become insoluble when temperature exceeds $T_t$.

In the present invention, the physicochemical properties of EBPs are mainly controlled by the combination of a pentapeptide repeat unit, Val-Pro-(Gly or Ala)-$X_{aa}$-Gly [VP (G or A)XG] (SEQ ID NO: 43). Specifically, the third amino acid of the repeat unit is responsible for determining the relative mechanical properties of EBPs. For example, according to the present invention, the third amino acid Gly is responsible for determining elasticity, or Ala is responsible for determining plasticity. Elasticity and plasticity are properties that appear after a transition occurs.

In addition, the hydrophobicity of a guest residue $X_{aa}$, the fourth amino acid, and multimerization of a pentapeptide repeat unit all affect $T_t$.

An EBP according to the present invention may be a polypeptide composed of pentapeptide repeats, and a polypeptide block, i.e., EBP block, may be formed when the polypeptide is repeated. Specifically, a hydrophilic or hydrophobic EBP block may be formed.

The hydrophilic or hydrophobic properties of an EBP block according to the present invention are closely related to the transition temperature of the EBP. The transition temperature of the EBP is also determined by the amino acid sequence of the EBP and molecular weight thereof. A number of studies on the relationship between EBP sequence and $T_t$ have been conducted by Urry et al (see Urry D. W., Luan C.-H., Parker T. M., Gowda D. C., Parasad K. U., Reid M. C., and Safavy A. 1991. TEMPERATURE OF POLYPEPTIDE INVERSE TEMPERATURE TRANSITION DEPENDS ON MEAN RESIDUE HYDROPHOBICITY. J. Am. Chem. Soc. 113: 4346-4348). According to the above reference, when, in a pentapeptide of Val-Pro-Gly-Val-Gly (SEQ ID NO: 44), the fourth amino acid, a "guest residue", is replaced with a residue that is more hydrophilic than Val, $T_t$ is increased compared to the original sequence. On the other hand, when the guest residue is replaced with a residue that is more hydrophobic than Val, $T_t$ is decreased compared to the original sequence. That is, it was found that a hydrophilic EBP has a high $T_t$ and a hydrophobic EBP has a relatively low $T_t$. Based on these findings, it has become possible to prepare an EBP having a specific $T_t$ by determining which amino acid is used as the guest residue of an EBP sequence and changing the composition ratio of the guest residue (see PROTEIN-PROTEIN INTERACTIONS: A MOLECULAR CLONING MANUAL, 2002, Cold Spring Harbor Laboratory Press, Chapter 18. pp. 329-343).

As described above, an EBP exhibits hydrophilicity when the EBP has a high $T_t$, and hydrophobicity when the EBP has a low $T_t$. Similarly, in the case of an EBP block according to the present invention, it is also possible to increase or decrease $T_t$ by changing an amino acid sequence including a guest residue and molecular weight. Thus, a hydrophilic or hydrophobic EBP block may be prepared.

For reference, an EBP having a $T_t$ lower than a body temperature may be used as a hydrophobic block, whereas an EBP having a $T_t$ higher than a body temperature may be used as a hydrophilic block. Due to this property of EBPs, the hydrophilic and hydrophobic properties of EBPs may be relatively defined when EBPs are applied to biotechnology.

Taking the sequence of an EBP of the present invention as an example, when a plastic polypeptide block in which a plastic pentapeptide of Val-Pro-Ala-$X_{aa}$-Gly (SEQ ID NO: 2) is repeated is compared with an elastic polypeptide block in which an elastic pentapeptide of Val-Pro-Gly-$X_{aa}$-Gly (SEQ ID NO: 1) is repeated, the third amino acid, Gly, has higher hydrophilicity than Ala. Accordingly, the plastic polypeptide block (elastin-based polypeptide with plasticity: EBPP) exhibits a lower $T_t$ than the elastic polypeptide block (elastin-based polypeptide with elasticity: EBPE).

EBPs according to the present invention, as described above, may exhibit hydrophilic or hydrophobic properties by adjusting $T_t$. In addition, as described below, in physical cross-linking (due to hydrophobic interactions) formed at or above the $T_t$ of a hydrophobic EBP, a structural change due to binding between the calcium of CalM and a ligand dynamically changes the three-dimensional structure of a hydrogel.

The polypeptide may have multi-stimuli responsiveness.

The term "multi-stimuli responsiveness" refers to responsiveness to one or more stimuli. Specifically, the stimuli may be one or more selected from the group including temperature, pH, ionic strength and a ligand.

In the present invention, a ligand is a substance that specifically binds to a target substance, and includes, for example, various antibodies, antigens, enzymes, substrates, receptors, peptides, DNA, RNA, aptamers, protein A, protein G, avidin, biotin, chelate compounds, and various metal ions (e.g., calcium ions).

In the present invention, the ligand may be calcium ions and/or a drug, but is not limited thereto.

In one embodiment, the present invention may include the following polypeptides:

[Val-Pro-Gly-Xaa-Gly]6 (SEQ ID NO: 45), that is, the pentapeptide repeats are 6 times, [VPGXG VPGXG VPGXG VPGXG VPGXG VPGXG (SEQ ID NO: 45)], and each Xaa of the pentapeptide repeats is consisted of A (Ala), G (Gly), and I (Ile) in a ratio of 1:4:1 [SEQ ID NO. 20];

each Xaa of the pentapeptide repeats is consisted of K (Lys), G (Gly), and I (Ile) in a ratio of 1:4:1 [SEQ ID NO. 22];

each Xaa of the pentapeptide repeats is consisted of D (Asp), G (Gly), and I (Ile) in a ratio of 1:4:1 [SEQ ID NO. 24];

each Xaa of the pentapeptide repeats is consisted of E (Glu), G (Gly), and I (Ile) in a ratio of 1:4:1 [SEQ ID NO. 26]; or each Xaa of the pentapeptide repeats is consisted of G (Gly), A (Ala), and F (Phe) in a ratio of 1:3:2 [SEQ ID NO. 28].

The ratio refers to the amino acid composition of $X_{aa}$ in the pentapeptide repeats.

Specifically, a nucleotide sequence corresponding to the polypeptide may be SEQ ID NO. 3 (a sequence corresponding to SEQ ID NO. 20), SEQ ID NO. 5 (a sequence corresponding to SEQ ID NO. 22), SEQ ID NO. 7 (a sequence corresponding to SEQ ID NO. 24), SEQ ID NO. 9 (a sequence corresponding to SEQ ID NO. 26) or SEQ ID NO. 11 (a sequence corresponding to SEQ ID NO. 28).

In another embodiment, the present invention may include the following polypeptides:

[Val-Pro-Ala-Xaa-Gly]6 (SEQ ID NO: 40), that is, the pentapeptide repeats are 6 times, [VPAXG VPAXG VPAXG VPAXG VPAXG VPAXG (SEQ ID NO: 40)], and each Xaa of the pentapeptide repeats is consisted of A (Ala), G (Gly), and I (Ile) in a ratio of 1:4:1 [SEQ ID NO. 21];

each Xaa of the pentapeptide repeats is consisted of K (Lys), G (Gly), and I (Ile) in a ratio of 1:4:1 [SEQ ID NO. 23];

each Xaa of the pentapeptide repeats is consisted of D (Asp), G (Gly), and I (Ile) in a ratio of 1:4:1 [SEQ ID NO. 25];

each Xaa of the pentapeptide repeats is consisted of E (Glu), G (Gly), and I (Ile) in a ratio of 1:4:1 [SEQ ID NO. 27];

each Xaa of the pentapeptide repeats is consisted of G (Gly), A (Ala), and F (Phe) in a ratio of 1:3:2 [SEQ ID NO. 29];

each Xaa of the pentapeptide repeats is consisted of K (Lys), A (Ala), and F (Phe) in a ratio of 1:3:2 [SEQ ID NO. 30];

each Xaa of the pentapeptide repeats is consisted of D (Asp), A (Ala), and F (Phe) in a ratio of 1:3:2 [SEQ ID NO. 31];

each Xaa of the pentapeptide repeats is consisted of K (Lys) and F (Phe) in a ratio of 3:3 [SEQ ID NO. 32];

each Xaa of the pentapeptide repeats is consisted of D (Asp) and F (Phe) in a ratio of 3:3 [SEQ ID NO. 33];

each Xaa of the pentapeptide repeats is consisted of H (His), A (Ala), and I (Ile) in a ratio of 3:2:1 [SEQ ID NO. 34];

each Xaa of the pentapeptide repeats is consisted of H (His) and G (Gly) in a ratio of 5:1 [SEQ ID NO. 35]; or each Xaa of the pentapeptide repeats is consisted of G (Gly), C (Cys), and F (Phe) in a ratio of 1:3:2 [SEQ ID NO. 36].

A nucleotide sequence corresponding to the polypeptide may be SEQ ID NO. 4 (corresponding to SEQ ID NO. 21), SEQ ID NO. 6 (corresponding to SEQ ID NO. 23), SEQ ID NO. 8 (corresponding to SEQ ID NO. 25), SEQ ID NO. 10 (corresponding to SEQ ID NO. 27), SEQ ID NO. 12 (corresponding to SEQ ID NO. 29), SEQ ID NO. 13 (corresponding to SEQ ID NO. 30), SEQ ID NO. 14 (corresponding to SEQ ID NO. 31), SEQ ID NO. 15 (corresponding to SEQ ID NO. 32), SEQ ID NO. 16 (corresponding to SEQ ID NO. 33), SEQ ID NO. 17 (corresponding to SEQ ID NO. 34), SEQ ID NO. 18 (corresponding to SEQ ID NO. 35) or SEQ ID NO. 19 (corresponding to SEQ ID NO. 36).

In accordance with an aspect of the present invention, the above and other objectives can be accomplished by the provision of a triblock polypeptide having multi-stimuli responsiveness, wherein the triblock polypeptide includes of, a calmodulin block; and polypeptide blocks having a phase transition behavior linked to both ends of the calmodulin block, and is represented by Formula 3 below:

[hydrophobic EBP]m-CalM-[hydrophobic EBP]m, wherein     Formula 3 the [hydrophobic EBP]m refers to a polypeptide block having a phase transition behavior; and the hydrophobic EBP is consisted of a hydrophobic polypeptide selected from the above-described polypeptides having a phase transition behavior;

m is an integer of 2 or more, and is the number of repeats of the hydrophobic polypeptide having a phase transition behavior; and the CalM is a calmodulin block.

In another embodiment, the present invention may provide a triblock polypeptide having multi-stimuli responsiveness, wherein a polypeptide block having a phase transition behavior further includes a [hydrophilic EBP] linked between the calmodulin block and the [hydrophobic EBP]m of Formula 3, and is represented by Formula 4:

[hydrophobic EBP]m-[hydrophilic EBP]x-CalM-[hydrophilic EBP]x-[hydrophobic EBP]m, wherein     Formula 4 the [hydrophobic EBP]m-[hydrophilic EBP]x and [hydrophilic EBP]x-[hydrophobic EBP]m refer to a polypeptide blocks having a phase transition behavior; and the hydrophobic EBP is consisted of a hydrophobic polypeptide selected from the above-described polypeptides having a phase transition behavior; and the hydrophilic EBP is consisted of a hydrophilic selected from the above-described polypeptides having a phase transition behavior; and;

m or x, each respectively, is an integer of 2 or more, and is the number of repeats of the hydrophobic polypeptide and hydrophilic polypeptide having a phase transition behavior; and the CalM is a calmodulin block.

A triblock polypeptide according to the present invention is an ABA-type triblock polypeptide. Triblock polypeptides in Formulas 3 and 4 are schematically shown in FIGS. 5A and 5B, respectively.

In EBP blocks constituting the triblock polypeptide and exhibiting a phase transition behavior, a hydrophobic EBP has a lower transition temperature than a hydrophilic EBP. An EBP is insoluble at or above a transition temperature ($T_t$ or LSCT). An ABA-type triblock polypeptide according to the present invention forms a physically cross-linked hydrogel by hydrophobic interactions due to the structural change of a hydrophobic EBP under physiological conditions at or above the $T_t$ of the hydrophobic EBP. In addition, the present invention may also control rheological and mechanical properties by introducing hydrophilic EBPs.

Since a transition temperature is changed by surrounding environmental conditions such as protein concentration, ionic strength and pH, the transition temperature is determined not as an absolute value but as a relative value. The present invention is related to the aspect of bioengineering. Accordingly, when the transition temperature of an EBP is lower than a body temperature, a triblock polypeptide according to the present invention exhibits hydrophobicity, whereas, when the transition temperature of an EBP is higher than a body temperature, the triblock polypeptide exhibits hydrophilicity. Thus, in the present invention, the hydrophilic and hydrophobic properties of an EBP may be relatively defined when the EBP is used in bioengineering. FIG. 4(F) is an example of an EBP according to the present invention exhibiting hydrophobicity. FIG. 4 shows that other EBPs exhibit hydrophilicity and the transition temperatures of the EBPs are varied under different ionic strength conditions.

In addition, since the calmodulin block has ligand responsiveness, conformational changes may occur when the calmodulin block binds to calcium ions and drugs. In addition, the conformational changes may be caused by dityrosine cross-linking formed by cross-linking of tyrosine residues within the calmodulin block. In addition, once the ligand is removed from the calmodulin, the original conformation of the calmodulin protein may be restored.

The calmodulin block refers to a block composed of calmodulin protein. Since the protein sequence of the calmodulin is already known in the art, any known calmodulin sequence may be used without limitation.

In addition, it is also within the scope of the present invention to use a modified calmodulin that has a partially modified sequence. In an embodiment of the present invention, GAG, a codon corresponding to Glu-83 of calmodulin, was mutated to GAA and the modified calmodulin was used (SEQ ID NO. 38).

In accordance with another aspect of the present invention, there is provided a triblock polypeptide having multi-stimuli responsiveness, wherein the triblock polypeptide includes of:

a calmodulin block; and polypeptide blocks having a phase transition behavior linked to both ends of the calmodulin block; and cysteine blocks linked to the polypeptide blocks, and is represented by Formula 5 below:

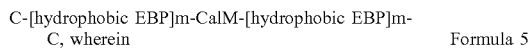

C-[hydrophobic EBP]m-CalM-[hydrophobic EBP]m-C, wherein          Formula 5 in Formula 5,

C is a cysteine block;

the [hydrophobic EBP]m refers to a polypeptide block having a phase transition behavior; and the hydrophobic EBP is consisted of a hydrophobic polypeptide selected from the above-described polypeptides having a phase transition behavior;

m is an integer of 2 or more, and is the number of repeats of the hydrophobic polypeptide having a phase transition behavior; and the CalM is a calmodulin block.

In another embodiment, the present invention may provide a triblock polypeptide having multi-stimuli responsiveness, wherein a polypeptide block having a phase transition behavior further includes a [hydrophilic EBP]m linked between the calmodulin block and the [hydrophobic EBP]m of Formula 5, and is represented by Formula 6 below:

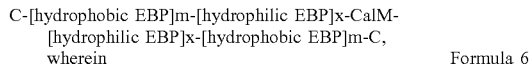

C-[hydrophobic EBP]m-[hydrophilic EBP]x-CalM-[hydrophilic EBP]x-[hydrophobic EBP]m-C, wherein          Formula 6 in Formula 6,

C is a cysteine block;

the [hydrophobic EBP]m-[hydrophilic EBP]x and -[hydrophilic EBP]x-[hydrophobic EBP]m refers to a polypeptide block having a phase transition behavior; and the hydrophobic EBP is consisted of a hydrophobic polypeptide selected from the above-described polypeptides having a phase transition behavior; and the hydrophilic EBP is consisted of a hydrophilic polypeptide selected from the above-described polypeptides having a phase transition behavior; and;

m or x, each respectively, is an integer of 2 or more, and is the number of repeats of the hydrophobic polypeptide and hydrophilic polypeptide having a phase transition behavior; and the CalM is a calmodulin block.

The cysteine block refers to a peptide sequence including cysteine. Specifically, the cysteine block may be composed of an amino acid sequence, in which (Gly-Ala-Cys) is repeated one or more times. More specifically, the cysteine block may include a peptide sequence composed of (Gly-Ala-Cys)n [n indicates the number of repetitions], but is not necessarily limited thereto.

In one embodiment of the present invention, a cysteine block having an amino acid sequence, Gly-Ala-Cys-Gly-Ala-Cys-Gly-Ala-Cys-Gly-Ala-Cys, which corresponds to [SEQ ID NO. 39], was used.

Triblock polypeptides in Formulas 5 and 6 are schematically shown in FIGS. 5C and 5D, respectively. EBP blocks having different molecular weights and different $T_t$s are arranged on both sides of a CalM block, and Cys blocks are introduced at both ends of the EBP blocks for chemical cross-linking.

As already described above, since EBP-CalM-EBP triblock polypeptides may reversibly exhibit thermally-triggered gelation, physical cross-linking of hydrophobic EBPs occurs under physiological conditions at or above $T_t$, resulting in formation of a physically cross-linked protein hydrogel. In addition, since a calmodulin block has ligand responsiveness, conformational changes may occur when the calmodulin block binds to calcium ions and/or a drug.

The stimuli are as described above. For example, the stimulus may be temperature or a ligand, but is not limited thereto.

In the triblock polypeptide, the polypeptide block having a phase transition behavior may exhibit thermal responsiveness, and the calmodulin block may exhibit ligand responsiveness.

According to one embodiment of the present invention, in the triblock polypeptide having multi-stimuli responsiveness, the [hydrophobic EBP]m may include of an amino acid sequence below:

[hydrophobic EBP]m, m is multiple of six, and the [hydrophobic EBP] is consisted of an amino acid sequence below:

Val-Pro-Ala-Xaa-Gly [SEQ ID NO. 40], wherein each Xaa of the pentapeptide repeats is consisted of G (Gly), A (Ala), and F (Phe) in a ratio of 1:3:2.

m may be 6, 12, 18, 24, 30 or 36, but is not limited thereto.

The [hydrophobic EBP]m is described in detail in the following embodiments (see Tables 1 and 2).

In another aspect of the present invention, depending on the unique combination of the pentapeptide repeats, various EBPs and block polypeptides thereof, which have unique physicochemical properties and $T_t$s, were prepared for stimuli-triggered micelle formation and hydrogelation.

Specifically, a hydrogel was prepared by a process including the following steps:

a step of applying a heat stimulus to a triblock polypeptide according to the present invention; and a step of cross-linking the hydrophobic EBPs of the triblock polypeptide by the heat stimulus and forming a hydrogel.

In another embodiment, the present invention may further include the following steps:

after the hydrophobic EBPs are cross-linked, a step of inducing a structural change of the calmodulin by specifically binding the calmodulin block, which constitutes the triblock polypeptide, to a ligand; and a step of forming a dynamic hydrogel by a three-dimensional structural change of the hydrogel induced by the structural change of the calmodulin block due to the ligand responsiveness.

In the step of cross-linking the hydrophobic EBPs, the cross-linking may be physical cross-linking that occurs at or above the transition temperature of the hydrophobic EBP.

In addition, the hydrogel may be formed by dityrosine cross-linking, which is generated by chemically cross-linking tyrosine residues within a calmodulin block constituting the triblock peptide.

In accordance with another aspect of the present invention, there is provided a hydrogel, wherein the hydrogel is prepared by the following process including:

a step of applying a heat stimulus to a triblock polypeptide according to Formula 5 or 6 below;

a step of cross-linking hydrophobic EBPs constituting the triblock polypeptide by the heat stimulus and forming a hydrogel; and a step of chemically cross-linking cysteine blocks constituting the triblock polypeptide.

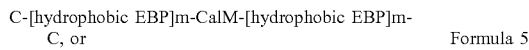
C-[hydrophobic EBP]m-CalM-[hydrophobic EBP]m-C, or                          Formula 5

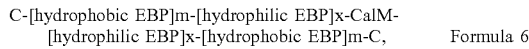
C-[hydrophobic EBP]m-[hydrophilic EBP]x-CalM-[hydrophilic EBP]x-[hydrophobic EBP]m-C,         Formula 6

Since description of Formulas 5 and 6 is the same as that described above, a detailed description thereof is omitted.

The stimuli are as described above. Specifically, the stimuli may be selected from the group consisting of temperature, pH, ionic strength and a ligand, but are necessarily limited thereto, and may be temperature and/or a ligand.

The term "hydrogel" according to the present invention generally refers to a material having a three-dimensional hydrophilic polymer network that may contain a large amount of water. The hydrogel is thermodynamically stable after swelling in an aqueous solution and has mechanical/physicochemical properties corresponding to an intermediate form of liquid and solid.

The hydrogel may be formed by cross-linking the thiol groups of cysteines within cysteine blocks constituting the triblock peptide.

The hydrogel may be formed by dityrosine cross-linking, which is generated by cross-linking tyrosine residues within a calmodulin block constituting the triblock peptide. Specifically, in one embodiment of the present invention, it was demonstrated that the tyrosine residues of the calmodulin block may be chemically cross-linked to form dityrosines via UV irradiation.

ABA-type EBP-CalM-EBP triblock polypeptides according to the present invention exhibit multi-stimuli responsiveness to temperature, calcium, and drug molecules, forming a dynamic protein hydrogel that is triggered by multi-stimuli. In addition, these dynamic protein hydrogels are useful in injectable drug delivery systems, functional tissue engineering, and regenerative medicine.

A triblock polypeptide according to the present invention is prepared by linking polypeptide blocks having thermal responsiveness and a calmodulin block having ligand responsiveness. Thus, in the triblock polypeptide according to the present invention, physical cross-linking may be formed at a temperature at or above the temperature corresponding to the biological environment, i.e., a temperature at or above $T_t$. In addition, in the triblock polypeptide, chemical crosslinking and physical crosslinking may occur simultaneously. In addition, the triblock polypeptide has calcium and ligand responsiveness. Therefore, a hydrogel using the triblock polypeptide according to the present invention has dynamic properties, and is a protein-based dynamic hydrogel that is a suitable injectable biomaterial and has stimuli-responsiveness.

In EBPs according to the present invention, physical cross-linking and chemical cross-linking occur at the same time. A variety of physically cross-linked EBP hydrogels have been developed for use as injectable biomaterials for drug delivery and storage, scaffolds for tissue engineering, and fillers for regenerative medicine. ABA-type triblock EBPs composed of a plastic EBP block having a low $T_t$ and an elastic EBP block having a high $T_t$ form physically cross-linked hydrogels at or above the low $T_t$ due to hydrophobic interactions between aggregated plastic EBP blocks. In addition, when triblock polypeptides including repeats of a plastic pentapeptide, Val-Pro-Ala-$X_{aa}$-Gly (SEQ ID NO: 2), were self-assembled via thermal transition, the triblock polypeptides exhibited higher mechanical properties than triblock polypeptides including repeats of an elastic pentapeptide, Val-Pro-Gly-$X_{aa}$-Gly (SEQ ID NO: 1). These physically cross-linked EBP triblocks may be applied to in vivo injectable systems. The present inventors also studied chemically cross-linked EBP hydrogels using various strategies including oxidation-reduction, UV or gamma irradiation, and covalent linkage via multi-functional linkers and enzymes. Since these chemically cross-linked EBP hydrogels exhibited improved mechanical properties over the physically cross-linked EBP hydrogels, the chemically cross-linked EBP hydrogels may be applied to cartilage tissue repair and vascular grafting.

The term "dynamic hydrogel' has the following meaning. A substance (e.g., protein) constituting a hydrogel may undergo a conformational change in response to a specific environmental condition, such as temperature, pH, ionic strength, and a ligand. In this case, the gel is called a "dynamic hydrogel".

Ligand binding-triggered conformational changes of proteins may be used to develop dynamic protein-based hydrogels because protein conformation changed by a ligand may be converted back to the natural conformation upon ligand removal. Specifically, calmodulin (CalM) with relative molecular mass of 17,000, a multi-functional intermediate messenger protein, is a calcium-binding protein including four high-affinity $Ca^{2+}$ binding sites with a $K_d$ (dissociation constant) in a range of 0.1 to 1 mM. When calcium ions bind to four helix-loop-helix motifs of CalM, the CalM protein undergoes a large conformational change, resulting in formation of dumbbell shaped structures at both ends of a long central helix. Furthermore, as the CalM associates with CalM-dependent proteins in the $Ca^{2+}$-bound state, the central helix of the CalM is warped. Likewise, the CalM in the $Ca^{2+}$-bound state undergoes a conformational change in the presence of certain ligand molecules such as phenothiazine derivatives and chlorpromazine. Finally, metal chelators including ethylenediaminetetraacetic acid (EDTA) and ethylene glycol-bis(β-aminoethyl ether)-N, N, N', N'-tetraacetic acid (EGTA) may remove all $Ca^{2+}$ and ligands bound to the CalM, and as a result, the CalM may return to the original state thereof.

As can be seen from the present invention, a three-dimensional change of a hydrogel occurs due to a dramatic conformational change in CalM, which is induced by $Ca^{2+}$ and a ligand bound to a CalM or removal of the $Ca^{2+}$ and ligand by metal chelators.

In accordance with another aspect of the present invention, there is provided a composition for drug delivery including the hydrogel.

Since the hydrogel responds to a ligand, a drug may be introduced into the hydrogel and be stably transferred to the body.

In accordance with another aspect of the present invention, there is provided a scaffold for tissue engineering including the hydrogel.

The scaffold for tissue engineering according to the present invention includes all scaffolds that may be used in the field of tissue engineering for the purpose of maintaining, enhancing or restoring the function of the body by preparing and implanting substitutes for living tissues.

In accordance with still another aspect of the present invention, there is provided a kit for tissue or organ regeneration including the hydrogel.

In the kit for tissue or organ regeneration according to the present invention, in addition to the scaffold for tissue engineering, a reinforcing layer for maintaining the shape of the scaffold may be added. The reinforcing layer may be selected from biodegradable polymer materials such as PCL, PLA, PLGA, and PGA.

The present invention provides a new class of dynamic protein hydrogels composed of genetically engineered ABA-type EBP-CalM-EBP triblock polypeptides.

In the following embodiments, a series of an ABA-type triblock polypeptide composed of multi-stimuli responsive elastin-based polypeptides (EBPs) and a ligand-responsive calmodulin (CalM) were genetically designed, expressed, and purified by inverse transition cycling (ITC) and based on the triblock polypeptides, multi-stimuli responsive dynamic protein hydrogels were prepared. For example, an EBP sequence with a pentapeptide repeat unit of Val-Pro-(Gly or Ala)-$X_{aa}$-Gly (SEQ ID NO: 43) was designed at the DNA level so that the fourth residue represented Gly, Ala, and Phe in a molar ratio of 1:3:2 and the $T_t$ at or below the physiological temperature was optimized. EBP blocks with amino acid composition ratios of $X_{aa}$ of pentapeptides which are differently repeated were arranged on both sides of a CalM block, and Cys blocks which are chemically cross-linkable domains were introduced at both ends of the EBP blocks. The EBP-CalM-EBP triblock polypeptides exhibited reversible thermally-triggered gelation, and based on this, physically crosslinked protein hydrogels were obtained at or above $T_t$ under physiological conditions, as characterized by rheological measurements. Furthermore, the physically crosslinked hydrogels of the EBP-CalM-EBP triblock polypeptides exhibited responsiveness to ligands for a CalM block, such as calcium and phenothiazine, a drug (ligand). Therefore, EBP-CalM-EBP triblock polypeptides exhibit multi-stimuli responsiveness to temperature, calcium, and ligand molecules, forming dynamic protein hydrogels that are triggered by the multi-stimuli. Potentially, these dynamic protein hydrogels may be useful in injectable drug delivery systems, functional tissue engineering, and regenerative medicine.

Stimuli-responsive protein-based biomaterials have been of great interest in the biomedical field because of stimuli-triggered self-assembly, superior biocompatibility, superior mechanical properties and specific biological functions thereof. In the following embodiments, a series of an ABA-type triblock polypeptide composed of thermally responsive elastin-based polypeptide blocks and a ligand-responsive calmodulin block were genetically designed, expressed, and purified by inverse transition cycling (ITC) and based on the triblock polypeptides, multi-stimuli responsive dynamic protein hydrogels were prepared. The EBP-CalM-EBP triblock polypeptides exhibited reversible thermally-triggered gelation, and as shown by rheological measurements, physically cross-linked protein hydrogels were formed above a transition temperature under physiological conditions. Furthermore, the physically crosslinked hydrogels of the EBP-CalM-EBP triblock polypeptides exhibited responsiveness to ligands for a CalM block, such as calcium and phenothiazine.

BRIEF DESCRIPTION OF THE DRAWINGS

The above and other objectives, features and advantages of the present invention will become more apparent to those of ordinary skill in the art by describing exemplary embodiments thereof in detail with reference to the accompanying drawings, in which.

DETAILED DESCRIPTION OF THE INVENTION

Example 1: Materials

Figure 1:
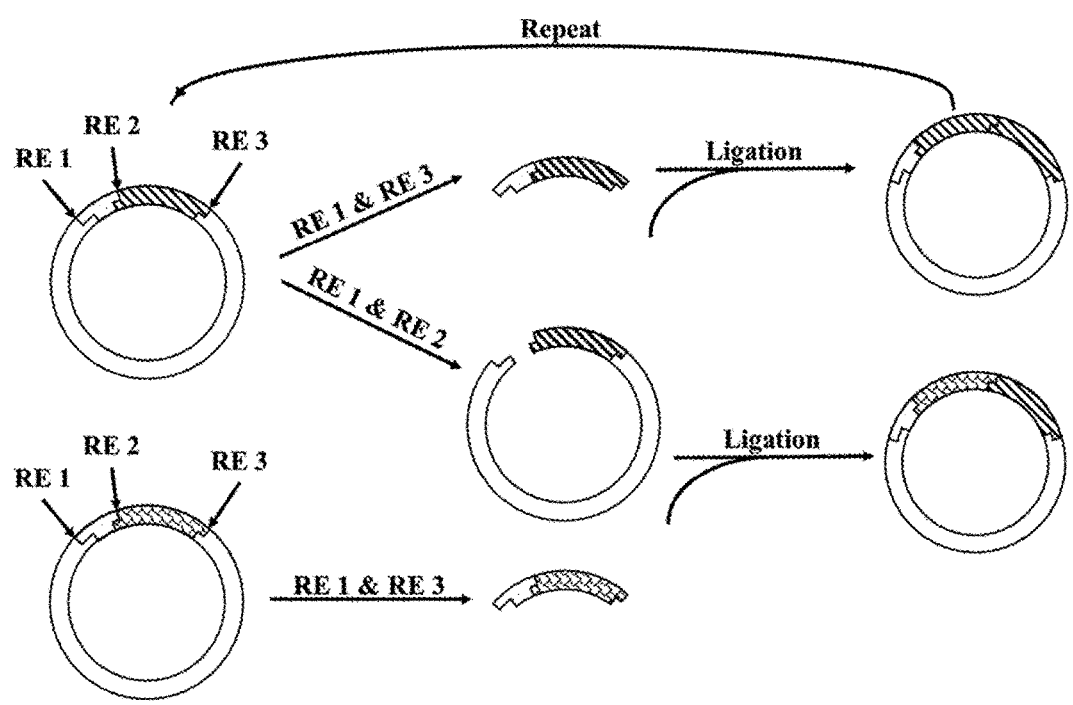
FIG. 1 is a schematic diagram showing construction of plasmids encoding EBP gene libraries with different DNA sizes and block polypeptides thereof. A modified vector was designed to include restriction sites recognized by three different restriction enzymes (REs), including XbaI (RE1), AcuI (RE2), and BseRI (RE3). For example, a gene construct encoding $EBPP[G_1A_3F_2]_{12}$ was prepared by a ligation reaction, in which a plasmid backbone and an insert derived from a plasmid-borne gene vector harboring a gene encoding $EBPP[G_1A_3F_2]_6$ were used: The plasmid-borne gene vector harboring a gene encoding $EBPP[G_1A_3F_2]_6$ was double-digested by XbaI and AcuI to obtain an insert, i.e., a gene fragment encoding $EBPP[G_1A_3F_2]_6$. On the other hand, the plasmid-borne gene vector for $EBPP[G_1A_3F_2]_6$ was double-digested by XbaI and BseRI to obtain a plasmid backbone and then the plasmid backbone was dephosphorylated by treatment with alkaline phosphatase.
Figure 2:
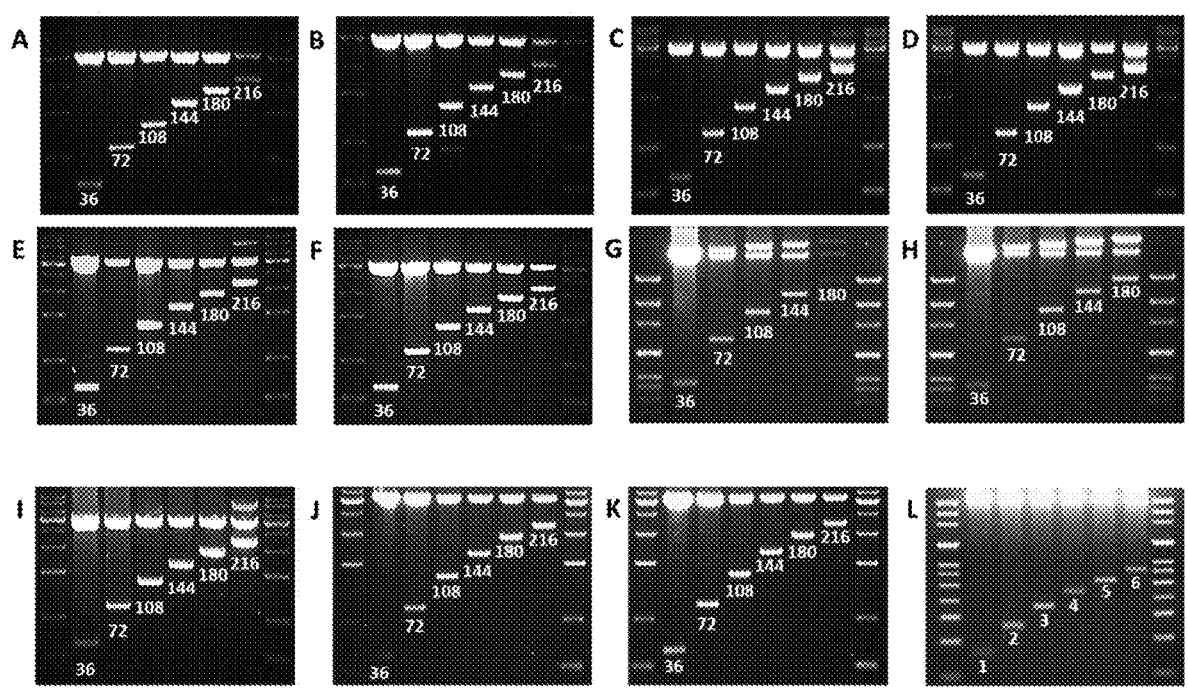
FIG. 2 shows agarose gel electrophoresis images of EBP gene libraries according to the present invention. (A) EBPE $[A_1G_4I_1]$, (B) EBPP$[A_1G_4I_1]$, (C) EBPE$[K_1G_4I_1]$, (D) EBPP$[K_1G_4I_1]$, (E) EBPE$[D_1G_4I_1]$, (F) EBPP$[D_1G_4I_1]$, (G) EBPE$[E_1G_4I_1]$, (H) EBPP$[E_1G_4I_1]$, (I) EBPP$[G_1A_3F_2]$, (J) EBPP$[K_1A_3F_2]$, (K) EBPP$[D_1A_3F_2]$, and (L) EBPP $[H_3A_2I_1]$. The number of EBP repeat units is indicated below each DNA band. The bilateral lanes on all agarose gels represent different DNA size markers (0.1, 0.2, 0.3, 0.4, 0.5, 0.6, 0.7, 1.0, 1.5, 2.0, and 3.0 kbp, from bottom to top)
Figure 3:
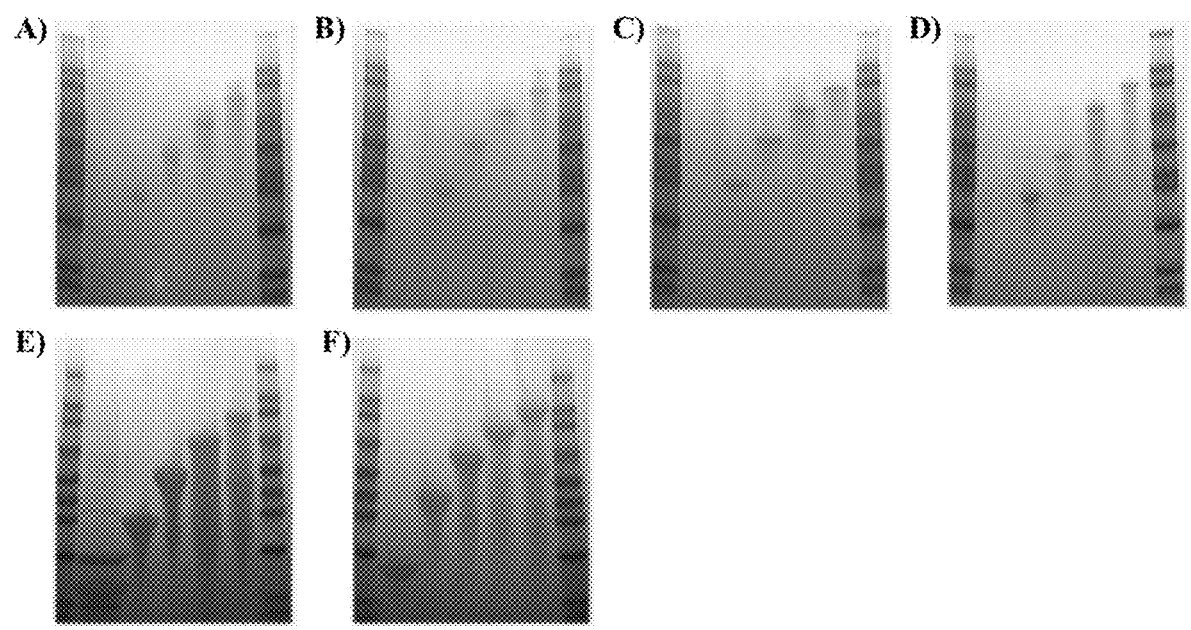
FIG. 3 shows copper-stained SDS-PAGE gel (4 to 20% gradient) images of EBPs according to the present invention. (A) EBPE$[A_1G_4I_1]$, (B) EBPP$[A_1G_4I_1]$, (C) EBPE$[K_1G_4I_1]$, (D) EBPP$[K_1G_4I_1]$, (E) EBPE$[D_1G_4I_1]$ and (F) EBPP $[D_1G_4I_1]$. Two-sided lanes on the SDS-PAGE gels contain standard protein size markers (7, 15, 24, 35, 40, 50, 65, 90, 110, and 150 kDa, from bottom to top)
Figure 4:
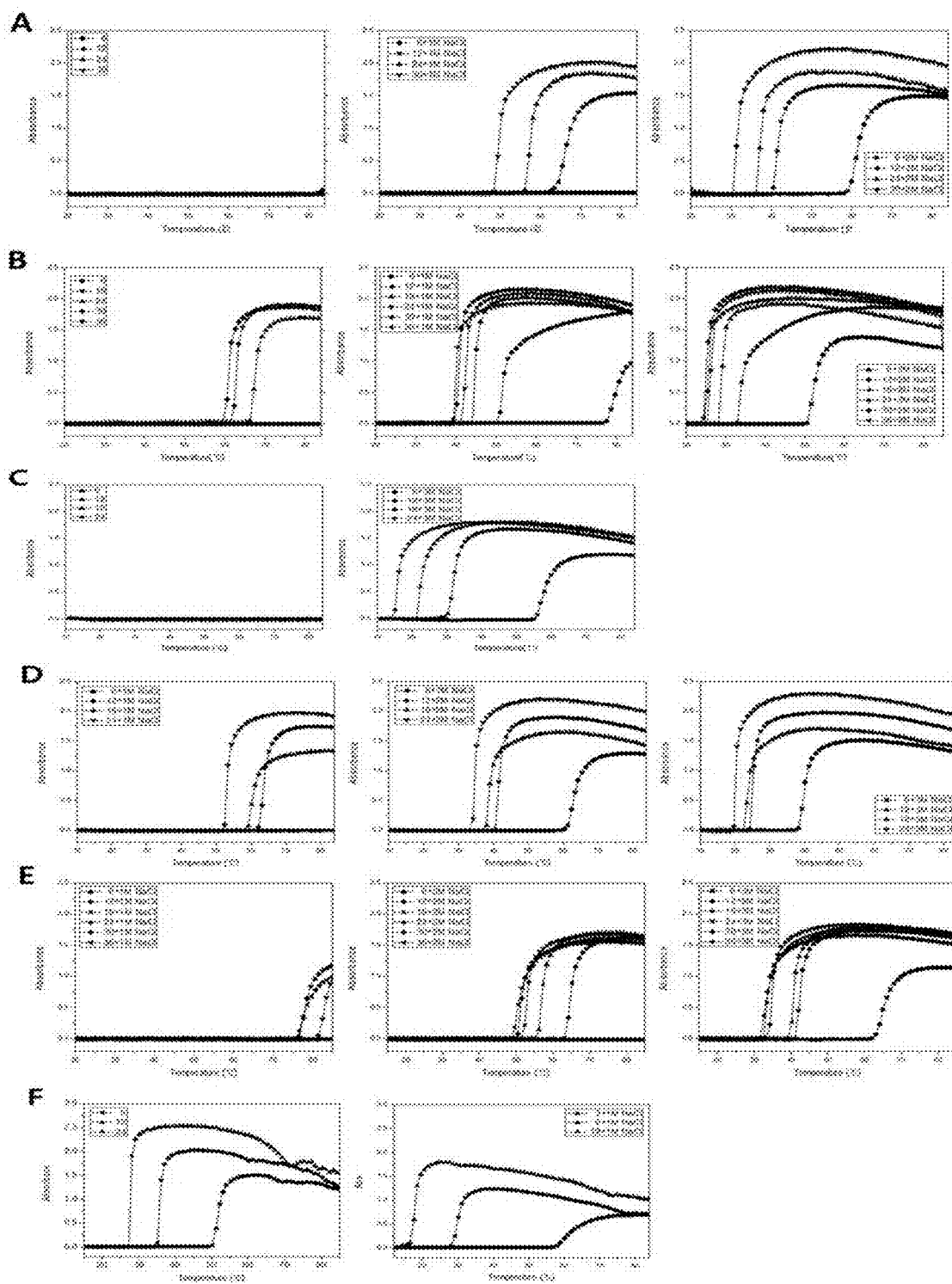
FIG. 4 shows the thermal profiles of EBPs according to the present invention. (A) EBPE$[A_1G_4I_1]_n$, (B) EBPP $[A_1G_4I_1]_n$, (C) EBPE$[K_1G_4I_1]_n$, (D) EBPP$[K_1G_4I_1]_n$, (E) EBPP$[D_1G_4I_1]_n$ and (F) EBPP$[G_1A_3F_2]_n$. To obtain thermal profiles, 25 μM EBP solutions were prepared in PBS buffer or PBS buffer supplemented with 1 to 3 M NaCl, and optical absorbance of the EBP solutions was measured at 350 nm while heating the solutions at a heating rate of 1° C./min.

A pET-21a vector and BL21 (DE3) *E. coli* cells were obtained from Novagen Inc. (Madison, Wis., U.S.). Top10 competent cells were obtained from Invitrogen (Carlsbad, Calif., U.S.). Oligonucleotides were chemically synthesized in Cosmo Gene Tech (Seoul, South Korea). FastAP, a thermosensitive alkaline phosphatase, and restriction endonucleases including BamHI and XbaI were purchased from Fermentas (Ontario, Canada). Other restriction endonucleases including BseRI, AcuI and other restriction enzymes were obtained from New England Biolabs (Ipswich, Mass., U.S.). T4 DNA ligase was obtained from Elpis Bio-tech (Taejeon, South Korea). All kits for DNA mini-preparation, gel extraction, and PCR purification were obtained from Geneall Biotechnology (Seoul, South Korea). Dyne Agarose High was obtained from DYNE BIO (Seongnam, South Korea). All Top10 cells were grown in TB DRY media (MO BIO Laboratories, Carlsbad, Calif., U.S.) and super optimal broth with catabolite repression (SOC) media (Formedium, UK) was supplemented with 20 mM glucose. All BL21 (DE3) cells were grown in Circlegrow media obtained from MP Biomedicals (Solon, Ohio, U.S.). Ready Gel (Tris-HCl, 2-20%), a precast gel, was obtained from Bio-Rad (Hercules, Calif., U.S.). Phosphate buffered saline (PBS, pH 7.4), ampicillin, polyethyleneimine (PEI), calcium chloride, ethylenediaminetetraacetic acid (EDTA), ethylene glycol-bis (β-aminoethyl ether)-N, N, N', N'-tetraacetic acid (EGTA), phenothiazine (PTZ), chlorpromazine (CPZ), and trifluoperazine (TFP) were obtained from Sigma-Aldrich (St Louis, Mo.).

Example 2: Notation for Different EBP Blocks and Block Polypeptides Thereof

Different EBPs having a pentapeptide repeat unit of Val-Pro-(Gly or Ala)-$X_{aa}$-Gly[VP (G or A)XG] (SEQ ID NO: 43) are named as follows. $X_{aa}$ may be any amino acid except Pro. First, pentapeptide repeats of Val-Pro-Ala-$X_{aa}$-Gly (VPAXG (SEQ ID NO: 2)) with plasticity are defined as an elastin-based polypeptide with plasticity (EBPP). On the other hand, pentapeptide repeats of Val-Pro-Gly-$X_{aa}$-Gly (VPGXG (SEQ ID NO: 1)) are called an elastin-based polypeptide with elasticity (EBPE). Second, in [$X_iY_jZ_k$]$_n$, the capital letters in the parentheses represent the single letter amino acid codes of guest residues, i.e., amino acids at the fourth position ($X_{aa}$ or X) of an EBP pentapeptide, and subscripts corresponding to the capital letters indicate the ratio of the guest residues in an EBP monomer gene as a repeat unit. The subscript number n of [$X_iY_jZ_k$]$_n$ represents the total number of repeats of an EBP. For example, EBPP [$G_1A_3F_2$]$_{12}$ is an EBPP block including 12 repeats of the Val-Pro-Gly-$X_{aa}$-Gly (SEQ ID NO: 1) pentapeptide unit, in which a ratio of Gly, Ala, and Phe at the fourth guest residue position ($X_{aa}$) is 1:3:2. Finally, the EBP-CalM-EBP triblock polypeptides are named by the composition of each block in square brackets with a hyphen between blocks such as EBPP[$G_1A_3F_2$]$_{12}$-CalM-EBPP[$G_1A_3F_2$]$_{12}$.

Example 3: Preparation of Modified pET-21a Vector for Cloning Seamless Gene

Four micrograms of a pET-21a vector was digested and dephosphorylated with 50 U of XbaI, 50 U of BamHI and 10 U of a thermosensitive alkaline phosphatase in FastDigest buffer for 20 minutes at 37° C. The restricted plasmid DNA was purified using a PCR purification kit, and then was eluted in 40 μl of distilled and deionized water. Two oligonucleotides with XbaI and BamHI compatible sticky ends were designed, i.e., SEQ ID NO. 40 (5'-ctagaaataattttgtt-taactttaagaaggaggagtacatatgggctactgataatgatcttcag-3') and SEQ ID NO. 41 (5'-gatcctgaagatcattatcagtagcc-catatgtactcctccttcttaaagttaaacaaaattattt-3'). To anneal the two types of oligonucleotides, each oligonucleotide was prepared at a concentration of 2 μM in 50 μl of T4 DNA ligase buffer, heat treated at 95° C. for 2 minutes and then slowly cooled to room temperature over 3 hours. To ligate the annealed dsDNA, i.e., a DNA insert, into multiple cloning sites within the linearized pET-21a vector, 20 pmol of the annealed dsDNA and 0.1 pmol of the linearized pET-21a vector were incubated in T4 DNA ligase buffer containing 1 U of T4 DNA ligase for 30 minutes at 37° C. The modified pET-21a (mpET-21a) vector for cloning and expressing a seamless gene was transformed into Top10 competent cells, followed by plating the Top10 competent cells on a super optimal broth with catabolite repression (SOC) plate supplemented with 50 μg/ml of ampicillin. The DNA sequence of the mpET-21a vector was then verified by fluorescent dye terminator DNA sequencing (Applied Biosystems Automatic DNA Sequencer ABI 3730).

Example 4: Synthesis of EBP Monomer Gene and Oligomerization Thereof

The EBP sequences having a pentapeptide repeat unit, Val-Pro-(Gly or Ala)-$X_{aa}$-Gly (SEQ ID NO: 43), in which the fourth residues were varied in different molar ratios, were designed at the DNA level to optimize $T_t$ below a physiological temperature. The DNA and amino acid sequences of EBPs with various pentapeptide repeat units for 17 EBP libraries are shown in Tables 1 and 2, respectively.

TABLE 1

Gene sequences corresponding to EBP libraries. Both EBPs with plasticity (EBPPs) having a pentapeptide repeat of Val-Pro-Ala-$X_{aa}$-Gly (SEQ ID NO: 2), and EBPs with elasticity (EBPEs) having a pentapeptide repeat of Val-Pro-Gly-$X_{aa}$-Gly (SEQ ID NO: 1) were all cloned to have the same guest residue composition and ratio.

| EBP | Gene Sequence | SEQ ID NO. |
|---|---|---|
| EBPE[$A_1G_4I_1$] | GTC CCA GGT GGA GGT GTA CCC GGC GCG GGT GTC CCA GGT GGA GGT<br>GTA CCT GGG GGT GGG GTC CCT GGT ATT GGC GTA CCT GGA GGC GGC | 3 |
| EBPP[$A_1G_4I_1$] | GTT CCA GCT GGC GGT GTA CCT GCT GCT GCT GTT CCG GCC GGT GGT<br>GTT CCG GCG GGC GGC GTG CCT GCA ATA GGA GTT CCC GCT GGT GGC | 4 |
| EBPE[$K_1G_4I_1$] | GTT CCG GGT GGT GGT GTT CCG GGT AAA GGT GTT CCG GGT GGT GGT<br>GTT CCG GGT GGT GGT GGT GTT CCG GGT ATC GGT GTT CCG GGT GGC | 5 |
| EBPP[$K_1G_4I_1$] | GTT CCG GCG GGT GGT GTT CCG GCG AAA GGT GTT CCG GCG GGT GGT<br>GTT CCG GCG GGT GGT GTT CCG GCG ATC GGT GTT CCG GCG GGT GGC | 6 |
| EBPE[$D_1G_4I_1$] | GTT CCG GGT GGT GGT GTT CCG GGT GAT GGT GTT CCG GGT GGT GGT<br>GTT CCG GGT GGT GGT GGT GTT CCG GGT ATC GGT GTT CCG GGT GGC | 7 |
| EBPP[$D_1G_4I_1$] | GTT CCG GCG GGT GGT GTT CCG GCG GAT GGT GTT CCG GCG GGT GGT<br>GTT CCG GCG GGT GGT GTT CCG GCG ATC GGT GTT CCG GCG GGT GGC | 8 |
| EBPE[$E_1G_4I_1$] | GTT CCG GGT GGT GGT GTT CCG GGT GAA GGT GTT CCG GGT GGT GGT<br>GTT CCG GGT GGT GGT GGT GTT CCG GGT ATC GGT GTT CCG GGT GGC | 9 |
| EBPP[$E_1G_4I_1$] | GTT CCG GCG GGT GGT GTT CCG GCG GAA GGT GTT CCG GCG GGT GGT<br>GTT CCG GCG GGT GGT GTT CCG GCG ATC GGT GTT CCG GCG GGT GGC | 10 |
| EBPE[$G_1A_3F_2$] | GTC CCG GGT GCG GGC GTG CCG GGA TTT GGA GTT CCG GGT GCG GGT<br>GTT CCA GGC GGT GGT GTT CCG GGC GCG GGC GTG CCG GGC TTT GGC | 11 |
| EBPP[$G_1A_3F_2$] | GTG CCG GCG GCG GGC GTT CCA GCC TTT GGT GTG CCA GCG GCG GGA<br>GTT CCG GCC GGT GGC GTG CCG GCA GCG GGC GTG CCG GCT TTT GGC | 12 |
| EBPP[$K_1A_3F_2$] | GTG CCG GCG GCG GGC GTT CCA GCC TTT GGT GTG CCA GCG GCG GGA<br>GTT CCG GCC AAA GGC GTG CCG GCA GCG GGC GTG CCG GCT TTT GGC | 13 |
| EBPP[$D_1A_3F_2$] | GTG CCG GCG GCG GGC GTT CCA GCC TTT GGT GTG CCA GCG GCG GGA<br>GTT CCG GCC GAT GGC GTG CCG GCA GCG GGC GTG CCG GCT TTT GGC | 14 |
| EBPP[$K_3F_3$] | GTT CCA GCG TTT GGC GTG CCA GCG AAA GGT GTT CCG GCG TTT GGG<br>GTT CCC GCG AAA GGT GTG CCG GCC TTT GGT GTG CCG GCC AAA GGC | 15 |
| EBPP[$D_3F_3$] | GTT CCA GCG TTT GGC GTG CCA GCG GAT GGT GTT CCG GCG TTT GGG<br>GTT CCC GCG GAT GGT GTG CCG GCC TTT GGT GTG CCG GCC GAT GGC | 16 |
| EBPP[$H_3A_3I_1$] | GTG CCG GCG CAT GGA GTT CCT GCC GCC GGT GTT CCT GCG CAT GGT<br>GTA CCG GCA ATT GGC GTT CCG GCA CAT GGT GTG CCG GCC GCC GGC | 17 |
| EBPP[$H_5G_1$] | GTT CCG GCC GGA GGT GTA CCG GCG CAT GGT GTT CCG GCA CAT GGT<br>GTG CCG GCT CAC GGT GTG CCT GCG CAT GGC GTT CCT GCG CAT GGC | 18 |
| EBPP[$G_1C_3F_2$] | GTG CCG GCG TGC GGC GTT CCA GCC TTT GGT GTG CCA GCG TGC GGA<br>GTT CCG GCC GGT GGC GTG CCG GCA TGC GGC GTG CCG GCT TTT GGC | 19 |

TABLE 2

Amino acid sequences corresponding to EBP libraries.

| EBP | Amino acid Sequence | SEQ ID NO. |
|---|---|---|
| EBPE[$A_1G_4I_1$] | VPGGG VPGAG VPGGG VPGGG VPGIG VPGGG | 20 |
| EBPP[$A_1G_4I_1$] | VPAGG VPAAG VPAGG VPAGG VPAIG VPAGG | 21 |
| EBPE[$K_1G_4I_1$] | VPGGG VPGKG VPGGG VPGGG VPGIG VPGGG | 22 |
| EBPP[$K_1G_4I_1$] | VPAGG VPAKG VPAGG VPAGG VPAIG VPAGG | 23 |
| EBPE[$D_1G_4I_1$] | VPGGG VPGDG VPGGG VPGGG VPGIG VPGGG | 24 |
| EBPP[$D_1G_4I_1$] | VPAGG VPADG VPAGG VPAGG VPAIG VPAGG | 25 |
| EBPE[$E_1G_4I_1$] | VPGGG VPGEG VPGGG VPGGG VPGIG VPGGG | 26 |
| EBPP[$E_1G_4I_1$] | VPAGG VPAEG VPAGG VPAGG VPAIG VPAGG | 27 |
| EBPE[$G_1A_3F_2$] | VPGAG VPGFG VPGAG VPGGG VPGAG VPGFG | 28 |
| EBPP[$G_1A_3F_2$] | VPAAG VPAFG VPAAG VPAGG VPAAG VPAFG | 29 |
| EBPP[$K_1A_3F_2$] | VPAAG VPAFG VPAAG VPAGG VPAAG VPAFG | 30 |
| EBPP[$D_1A_3F_2$] | VPAAG VPAFG VPAAG VPAGG VPAAG VPAFG | 31 |
| EBPP[$K_3F_3$] | VPAFG VPAKG VPAFG VPAKG VPAFG VPAKG | 32 |
| EBPP[$D_3F_3$] | VPAFG VPADG VPAFG VPADG VPAFG VPADG | 33 |
| EBPP[$H_3A_3I_1$] | VPAHG VPAAG VPAHG VPAIG VPAHG VPAAG | 34 |
| EBPP[$H_5G_1$] | VPAGG VPAHG VPAHG VPAHG VPAHG VPAHG | 35 |
| EBPP[$G_1C_3F_2$] | VPACG VPAFG VPACG VPAGG VPACG VPAFG | 36 |

In Table 1, SEQ ID NO. 3 to 10 may be classified as gene sequences for hydrophilic EBP blocks, and SEQ ID NO. 11 to 19 may be classified as gene sequences for hydrophobic EBP blocks, in which Phe and His are incorporated. That is, as described above, when the LCST of an EBP is lower than the body temperature, the EBP exhibits hydrophobicity, and when the LCST of an EBP is higher than the body temperature, the EBP exhibits hydrophilicity. Due to this property of EBPs, the hydrophilic and hydrophobic properties of EBPs may be relatively defined when EBPs are applied to biotechnology.

Different EBPs having a pentapeptide repeat unit, Val-Pro-(Gly or Ala)-$X_{aa}$-Gly (SEQ 10 ID NO: 43) [where $X_{aa}$ may be any amino acid except Pro], which are capable of responding to unique stimuli including temperature and pH, were designed at the DNA level. EBPs with plasticity (EBPPs) having a pentapeptide repeat unit of Val-Pro-Ala-$X_{aa}$-Gly (SEQ ID NO: 2) and EBPs with elasticity (EBPEs) having a pentapeptide repeat unit of Val-Pro-Gly-$X_{aa}$-Gly (SEQ ID NO: 1) were all cloned to have the same guest residue composition and ratio. Tables 1 and 2 represent the gene and amino acid sequences of different EBPs having respective pentapeptide repeat units. For example, EBPE [$G_1A_3F_2$]$_{12}$ and EBPP[$G_1A_3F_2$]$_{12}$ not only show almost the same molar mass, but also the fourth residues of these EBP pentapeptide repeat units represent the same combination. In addition, these EBP blocks have different mechanical properties because the third amino acid residue (Ala or Gly) of the pentapeptide repeat units are different. Positively and negatively charged EBPs were constructed by introducing charged amino acids such as Lys, Asp, Glu, His and the like as guest residues.

To anneal each pair of oligonucleotides encoding various EBPs, each oligonucleotide was prepared at a concentration of 2 µM in 50 µl of T4 DNA ligase buffer, heat treated at 95° C. for 2 minutes and then slowly cooled to room temperature over 3 hours. Four micrograms of a modified pET-21a (mpET-21a) vector was digested and dephosphorylated with 15 U of BseRI and 10 U of FastAP thermosensitive alkaline phosphatase for 30 minutes at 37° C. The restricted plasmid DNA was purified using a PCR purification kit, and then was eluted in 40 µl of distilled and deionized water. To ligate the annealed dsDNA, i.e., a DNA insert, into multiple cloning sites within the linearized mpET-21a vector, 90 pmol of the annealed dsDNA and 30 pmol of the linearized mpET-21a vector were incubated in T4 DNA ligase buffer containing 1 U of T4 DNA ligase for 30 minutes at 16° C. The ligated plasmid was transformed into Top10 chemically competent cells, followed by plating the Top10 competent cells on a SOC plate supplemented with 50 µg/ml of ampicillin. DNA sequences was then verified by DNA sequencing. After all EBP monomer genes were constructed, each EBP gene was synthesized by ligating each of 36 types of repetitive genes (as an insert) into the corresponding vector containing each of the same 36 types of repetitive genes, as follows. A cloning procedure for EBP libraries and fusions thereof is illustrated in FIG. 1. Vectors harboring gene copies corresponding to EBP monomers were digested and dephosphorylated with 10 U of XbaI, 15 U of BseRI and 10 U of FastAP thermosensitive alkaline phosphatase in CutSmart buffer for 30 minutes at 37° C. The restricted plasmid DNA was purified using a PCR purification kit, and then was eluted in 40 µl of distilled and deionized water. For preparation of an insert part, a total of 4 µg of an EBP monomer gene were digested with 10 U of XbaI and 15 U of AcuI in CutSmart buffer for 30 minutes at 37° C. After digestion, the reaction product was separated by agarose gel electrophoresis and the insert was purified using a gel extraction kit. A ligation reaction was performed by incubating 90 pmol of the purified insert with 30 pmol of the linearized vector in T4 DNA ligase buffer containing 1 U of T4 DNA ligase for 30 minutes at 16° C. The product was transformed into Top10 chemically competent cells, then the cells were plated on a SOC plate supplemented with 50 µg/ml of ampicillin. Transformants were initially screened by a diagnostic restriction digest on an agarose gel and further confirmed by DNA sequencing as described above.

As described above, EBP gene libraries having different DNA sizes were synthesized using the designed plasmid vector and three different restriction endonucleases. FIG. 1 illustrates a recursive directional ligation (RDL) method, in which EBP monomer genes are ligated to form oligomerized EBP genes. For example, a gene construct encoding EBPP [$G_1A_3F_2$]$_2$ was prepared by a ligation reaction, in which a plasmid backbone and an insert derived from a plasmid-borne gene vector harboring a gene encoding EBPP [G₁A₃F₂]₆ were used: The plasmid-borne gene vector harboring a gene encoding EBPP[G₁A₃F₂]₆ was double-digested by XbaI and AcuI to obtain an insert, i.e., a gene fragment encoding EBPP[G₁A₃F₂]₆. On the other hand, the

TABLE 3-continued

Gene (SEQ ID NO. 37) and amino acid (SEQ ID
NO. 38) sequences of calmodulin (CalM)

| AGA | TCG | CTG | GGG | CAA | AAC | CCC | ACT | GAG | GCG | GAA | CTG |
|---|---|---|---|---|---|---|---|---|---|---|---|
| R | S | L | G | Q | N | P | T | E | A | E | L |

| CAG | GAC | ATG | ATC | AAT | GAG | GTG | GAT | GCT | GAT | GGC | AAT |
|---|---|---|---|---|---|---|---|---|---|---|---|
| Q | D | M | I | N | E | V | D | A | D | G | N |

| GGG | ACC | ATT | GAC | TTC | CCA | GAG | TTC | CTG | ACC | ATG | ATG |
|---|---|---|---|---|---|---|---|---|---|---|---|
| G | T | I | D | F | P | E | F | L | T | M | M |

| GCC | AGA | AAG | ATG | AAG | GAT | ACA | GAC | AGC | GAG | GAA | GAG |
|---|---|---|---|---|---|---|---|---|---|---|---|
| A | R | K | M | K | D | T | D | S | E | E | E |

| ATA | CCA | GAG | GCC | TTC | CGT | GTC | TTT | GAC | AAG | GAT | GGG |
|---|---|---|---|---|---|---|---|---|---|---|---|
| I | P | E | A | F | R | V | F | D | K | D | G |

| AAT | GGC | TAC | ATC | AGT | GCT | GCT | GAG | CTG | CGT | CAC | GTC |
|---|---|---|---|---|---|---|---|---|---|---|---|
| N | G | Y | I | S | A | A | E | L | R | H | V |

| ATG | ACG | AAC | CTG | GGG | GAG | AAG | CTG | ACT | GAT | GAG | GAA |
|---|---|---|---|---|---|---|---|---|---|---|---|
| M | T | N | L | G | E | K | L | T | D | E | E |

| GTG | GAT | GAG | ATG | ATC | CGA | GAG | GCG | GAC | ATT | GAT | GGA |
|---|---|---|---|---|---|---|---|---|---|---|---|
| V | D | E | M | I | R | E | A | D | I | D | G |

| GGC | GGC | CAG | GTC | AAT | TAT | GAA | GAG | TTT | GTA | CAG | ATG |
|---|---|---|---|---|---|---|---|---|---|---|---|
| G | G | Q | V | N | Y | E | E | F | V | Q | M |

| ATG | ACT |
|---|---|
| M | T |

※ Area marked in bold is mutated region, and underlined representation is dityrosine binding region

Example 6: Gene Construction of EBP-CalM-EBP Triblock Polypeptide

Each plasmid containing EBP, CalM, or a Cys-incorporated block was used to prepare genes for the fusion polypeptide libraries of EBP[$G_1A_3F_2$]$_n$-CalM-EBP[$G_1A_3F_2$]$_n$ with Cys blocks at both ends. A plasmid vector harboring an EBP gene was digested and dephosphorylated with 10 U of XbaI, 10 U of BseRI and 10 U of FastAP, a thermosensitive alkaline phosphatase, in CutSmart buffer for 30 minutes at 37° C. The restricted plasmid DNA was purified using a PCR purification kit, and then was eluted in 40 µl of distilled and deionized water. A total of 4 µg of the CalM gene was digested with 10 U of XbaI and 15 U of AcuI in the CutSmart buffer for 30 minutes at 37° C. to prepare the CalM gene as an insert, followed by separation using agarose gel electrophoresis and purification using a gel extraction kit. A ligation reaction was performed by incubating 90 pmol of the purified insert with 30 pmol of the linearized vector in T4 DNA ligase buffer containing 1 U of T4 DNA ligase for 30 minutes at 16° C. The product was transformed into Top10 chemically competent cells, then the cells were plated on a SOC plate supplemented with 50 µg/ml of ampicillin. Transformants were initially screened by a diagnostic restriction digest on an agarose gel and further confirmed by DNA sequencing as described above.

Example 7: Gene Expression and Purification of EBPs and Block Polypeptides Thereof E. coli strain BL21(DE3) cells were transformed with each vector containing an EBP or EBP block polypeptide, and then inoculated in 50 ml of CircleGrow media supplemented with 50 µg/ml ampicillin. Preculturing was performed in a shaking incubator at 200 rpm overnight at 37° C. 50 ml of CircleGrow media was then inoculated in 500 ml of CircleGrow media with 50 µg/ml ampicillin and incubated in a shaking incubator at 200 rpm for 16 hours at 37° C. When optical density at 600 nm ($OD_{600}$) reached 1.0, overexpression of an EBP gene or a block polypeptide gene thereof was induced by addition of IPTG at a final concentration of 1 mM. The cells were centrifuged at 4500 rpm for 10 minutes at 4° C. The expressed EBPs and block polypeptides thereof were purified by inverse transition cycling (ITC) as reported previously (see Dong Woo Lim, Kimberly Trabbic-Carlson, J. Andrew MacKay and Ashutosh Chilkoti, "IMPROVED NON-CHROMATOGRAPHIC PURIFICATION OF A RECOMBINANT PROTEIN BY CATIONIC ELASTIN-LIKE POLYPEPTIDES", Biomacromolecules, 8 (5), 1417-1424, 2007). The cell pellet was resuspended in 30 ml of HEPES buffer, and the cells were lysed by sonication for 10 s at 20 s intervals (VC-505, Sonics & Materials Inc, Danbury, Conn.) on an ice bath. The cell lysate was centrifuged in a 50 ml centrifuge tube at 13000 rpm for 15 min at 4° C. to precipitate the insoluble debris of the cell lysate. A supernatant containing water soluble EBPs was then transferred to a new 50 ml centrifuge tube and centrifuged with 0.5% w/v of PEI at 13000 rpm for 15 minutes at 4° C. to precipitate nucleic acid contaminants. The inverse phase transition of the EBPs were triggered by adding sodium chloride at a final concentration of 3 to 4 M, and the aggregated EBPs were separated from the lysate solution by centrifugation at 13000 rpm for 15 minutes at 37° C. The aggregated EBPs were resuspended in cold HEPES buffer, and the EBP solutions were centrifuged at 13000 rpm for 15 minutes at 4° C. to remove any aggregated protein contaminants. These aggregation and resuspension processes were repeated 5 to 10 times until the purity of EBP reached approximately 95%, as determined by SDS-PAGE and gel permeating chromatography with a high-performance liquid chromatography (HPLC) 1260 series instrument (Agilent Technologies, Palo Alto, Calif., USA) using Shodex GPC column OHpak SB-804 HQ (Showa Denko Co., Tokyo, Japan). Deionized water at 20° C. was used as an eluent at a flow rate of 1 ml/min and a GPC column was maintained at 20° C. A low-dispersity pullulan in the range of 5900 to 200000 g/mol was used as a standard. The EBPs and the block copolypeptides thereof were analyzed with a refractive index detector (RID) and a variable wavelength detector (VWD) at 280 nm. An effect of temperature on inverse phase transition of the various EBPs and the block polypeptides thereof at 25 µM concentration in HEPES buffer was determined by measuring $OD_{350}$ using a Cary 100 Bio UV/Vis Spectrophotometer equipped with a multi-cell thermoelectric temperature controller (Varian Instruments, Walnut Creek, Calif.) at 10 to 85° C. at a rate of 1° C./min.

Figure 5:
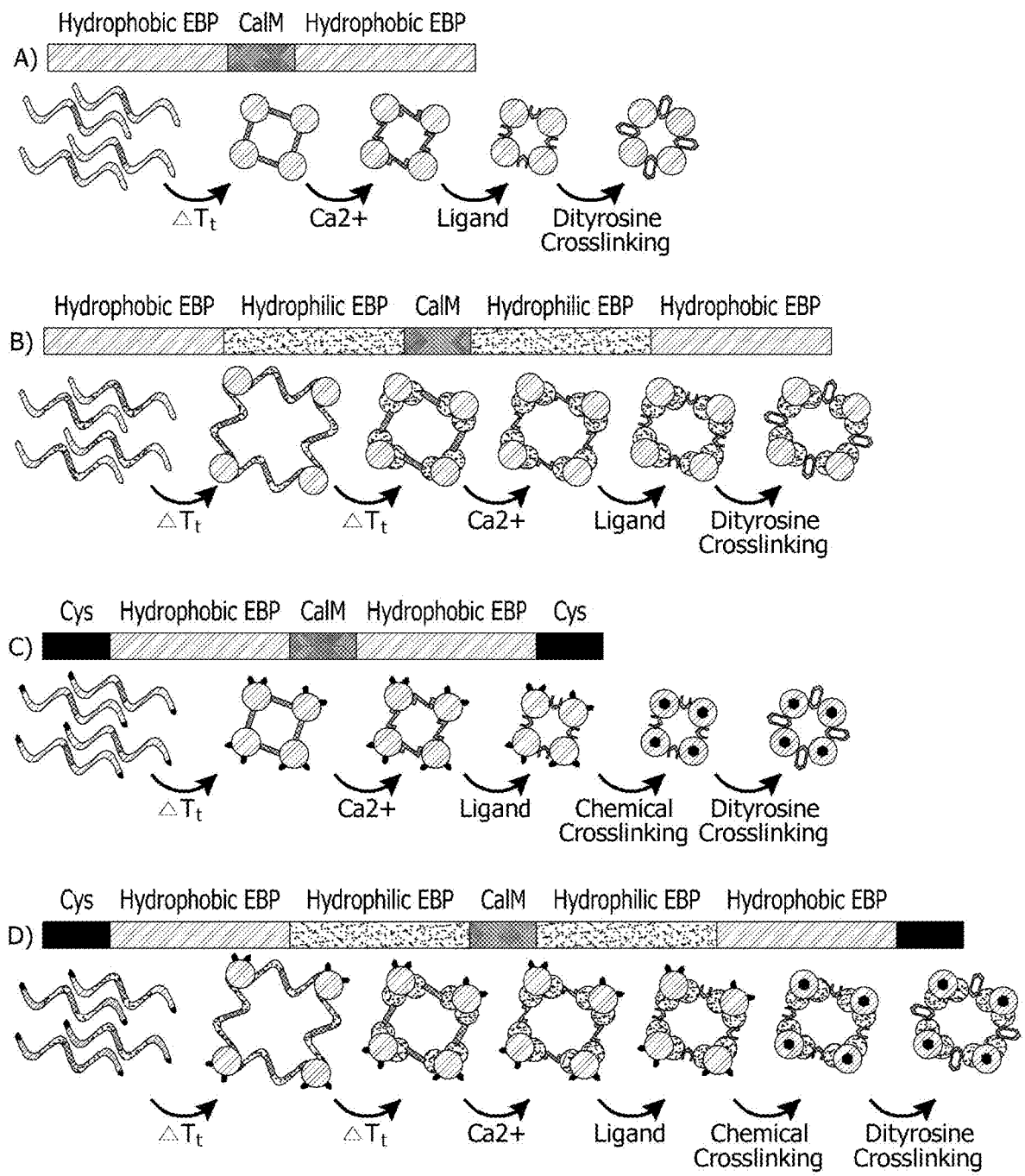
FIG. 5 shows schematic diagrams of dynamic protein hydrogels composed of genetically engineered ABA-type EBP-CalM-EBP triblock polypeptides. Two different types of EBP blocks, such as a hydrophobic EBP having a low $T_t$ and a hydrophilic EBP having a high $T_t$, were introduced. (A) hydrophobic EBP-CalM-hydrophobic EBP, (B) hydrophobic EBP-hydrophilic EBP-CalM-hydrophilic EBP-hydrophobic EBP, (C) Cys block-hydrophobic EBP-CalM-hydrophobic EBP-Cys block, and (D) Cys block-hydrophobic EBP-hydrophilic EBP-CalM-hydrophilic EBP-hydrophobic EBP-Cys block.

FIG. 5 shows schematic diagrams of dynamic protein hydrogels composed of genetically engineered ABA-type EBP-CalM-EBP triblock polypeptides. Two different types of EBP blocks, such as a hydrophobic EBP having a low $T_t$ and a hydrophilic EBP having a high $T_t$, were introduced. A series of EBP-CalM-EBP triblock polypeptides in FIG. 5 were designed as follows: (A) hydrophobic EBP-CalM-hydrophobic EBP, (B) hydrophobic EBP-hydrophilic EBP-CalM-hydrophilic EBP-hydrophobic EBP, (C) Cys block-hydrophobic EBP-CalM-hydrophobic EBP-Cys block, and (D) Cys block-hydrophobic EBP-hydrophilic EBP-CalM-hydrophilic EBP-hydrophobic EBP-Cys block. EBP blocks having different molecular weights and different $T_t$s were arranged on both sides of the CalM block, and Cys blocks were introduced at both ends of the EBP blocks for chemical cross-linking. Since EBP-CalM-EBP triblock polypeptides may reversibly exhibit thermally initiated gelation, a physically cross-linked protein hydrogel may be generated under physiological conditions at or above $T_t$. In addition, an EBP-CalM-EBP triblock polypeptide may form a physically cross-linked protein hydrogel under aqueous solution conditions above the transition temperature of a hydrophobic EBP, and ligands such as calcium and a phenothiazine drug specifically bind to CalM, thereby inducing a structural change in CalM to dynamically change the three-dimensional network of the hydrogel. Furthermore, the thiol groups of Cys blocks at both ends may be chemically crosslinked via oxidation, and Tyr residues in the CalM block may be also chemically crosslinked into dityrosine via UV irradiation. Depending on multi-responsiveness of the EBP-CalM-EBP triblock polypeptides, physicochemical and mechanical properties thereof may be finely controlled. Consequently, EBP-CalM-EBP triblock polypeptides exhibit multi-stimuli responsiveness to temperature, calcium, and ligand molecules, forming a dynamic protein hydrogel that is triggered by the multi-stimuli.

Example 8: Rheological Measurement of Physically and Chemically Cross-Linked Hydrogels EBP-CalM-EBP triblock polypeptide solutions were prepared in different HEPES buffers supplemented with various concentrations of oxidizing and reducing agents, $CaCl_2$, or phenothiazine as ligands for CalM. The EBP-CalM-EBP solutions were studied in dynamic-shear rheological testing (cone-and-plate configuration, cone angle=1.58°, diameter=20 mm, TA DHR1 with Peltier plate, TA instruments, Inc., U.S.) to quantify the elastic modulus (G'), loss modulus (G"), complex shear modulus (G*), complex viscosity ($\eta$*), and loss angle ($\delta$) as functions of temperature and frequency. The G' characterizes the elastic behavior of a material whereas the G" characterizes the viscous behavior of the material. The G* and $\eta$* represent the frequency-dependent stiffness, and the frequency-dependent viscous drag of a viscoelastic liquid or solid, respectively. The loss angle ($\delta$) is a relative measure of viscous to elastic properties (Newtonian viscous fluid: $\delta$=90°; elastic solid: $\delta$=0°). A metal solvent trap under fully hydrating conditions was used to prevent solvent evaporation over temperatures ranging from 10 to 40° C. All samples were equilibrated for at least 5 to 10 minutes at the desired temperatures prior to each experiment. Dynamic frequency sweep measurements were performed in the linear viscoelastic regime at different temperatures, as confirmed by independent strain sweep tests (strain sweep range: 0.2 to 20%, angular frequency: 0.1 or 10 rad/s). The angular frequency ranged from 0.1 to 10 rad/s, both at 10° C. (below $T_t$) and 40° C. (above $T_t$) for the frequency sweep tests.

The temperature sweep tests were executed with 2% strain at 1 rad/s over a temperature range of 10 to 40° C. with one minute in duration per degree for forward heating and reverse cooling measurements to examine the reversibility of rheological and mechanical properties thereof. The storage modulus (G'), the loss modulus (G"), the complex shear modulus (G*), the complex viscosity ($\eta$*), and the loss angle ($\delta$) were obtained from each oscillatory shear measurement. Each experiment was performed three times to ensure reproducibility.

Figure 6:
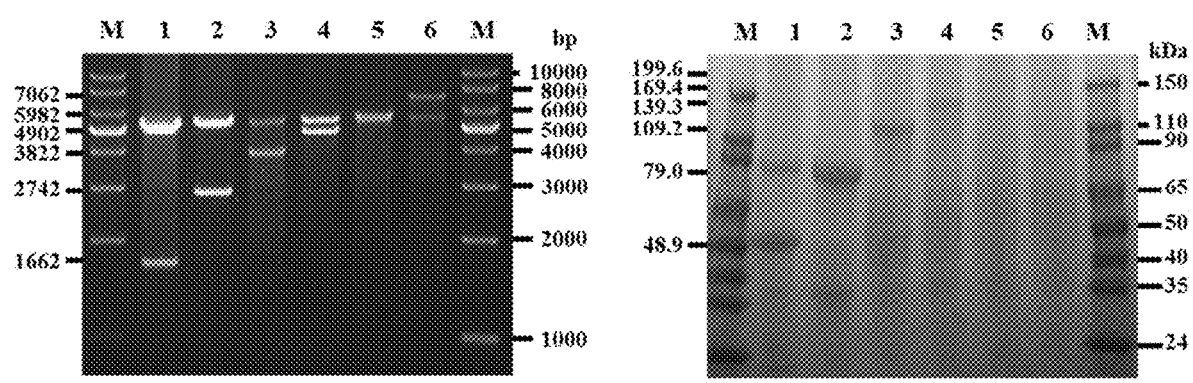
FIG. 6 shows the DNA agarose gel electrophoresis (0.8%) images (left) and the copper-stained SDS-PAGE (4-20% gradient) gel images (right) of a series of constructed Cys-EBPP[$G_1A_3F_2$]$_{6n}$-CalM-EBPP[$G_1A_3F_2$]$_{6n}$-Cys (n: integer). Each lane of the gel on either side represents (1) Cys block-EBPP[$G_1A_3F_2$]$_6$-CalM-EBPP[$G_1A_3F_2$]$_6$-Cys block, (2) Cys block-EBPP[$G_1A_3F_2$]$_{12}$-CalM-EBPP[$G_1A_3F_2$]$_{12}$-Cys block, (3) Cys block-EBPP[$G_1A_3F_2$]$_{18}$-CalM-EBPP[$G_1A_3F_2$]$_{18}$-Cys block, (4) Cys block-EBPP[$G_1A_3F_2$]$_{24}$-CalM-EBPP[$G_1A_3F_2$]$_{24}$-Cys block, (5) Cys block-EBPP[$G_1A_3F_2$]$_{30}$-CalM-EBPP[$G_1A_3F_2$]$_{30}$-Cys block, and (6) Cys block-EBPP[$G_1A_3F_2$]$_{36}$-CalM-EBPP[$G_1A_3F_2$]$_{36}$-Cys block.

Hydrophobic $EBPP[G_1A_3F_2]$ blocks with various molecular weights (M.W.) was introduced into the Cys block-hydrophobic EBP-CalM-hydrophobic EBP-Cys block at the DNA level. A DNA agarose gel electrophoresis image in FIG. 6 (left) clearly shows the different DNA sizes of a series of constructed Cys block-$EBPP[G_1A_3F_2]_{6n}$-CalM-$EBPP[G_1A_3F_2]_{6n}$-Cys block (n: integer) in the range of 1596, 2676, 3756, 4836, 5916, and 6996 base pairs (bps) from the first to sixth lane. The triblock polypeptides were overexpressed in E. coli and purified by ITC as described above. A copper-stained SDS-PAGE gel in FIG. 6 (right) shows that these triblock polypeptides were purified to at least 95% homogeneity by five to six rounds of ITC, as characterized by GPC analysis. The theoretical molecular weights of the polypeptides shown on the right of the gel in FIG. 6 (right) are 49.0, 79.1, 109.2, 139.4, 169.5, and 199.6 kDa from the first to sixth lane. It was found that the polypeptides were partly oxidized during SDS-PAGE, indicating dimers formed via disulfide bridges.

Figure 7:
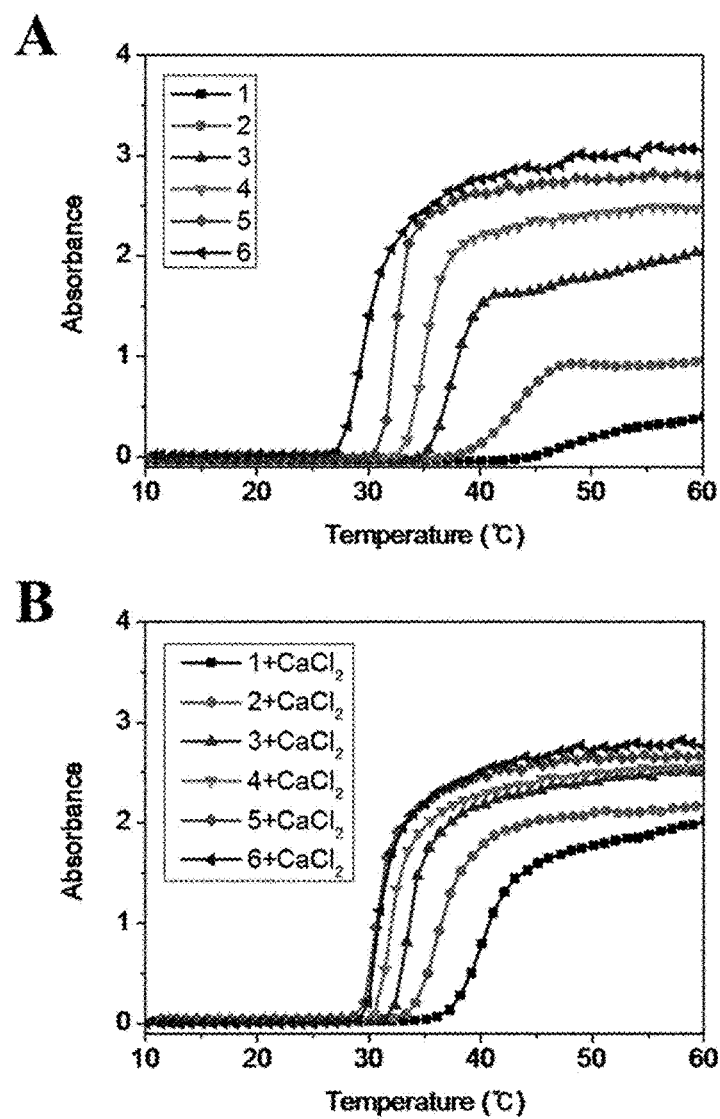
FIG. 7 shows the thermal profiles of Cys block-EBPP[$G_1A_3F_2$]$_{6n}$-CalM-EBPP[$G_1A_3F_2$]$_{6n}$-Cys block in 10 mM HEPES buffer at pH 7.4 (A) and in 10 mM HEPES buffer supplemented with 10 mM $CaCl_2$ (B), when characterized by turbidity profiling as a function of temperature at a heating rate of 1° C./min. Each number in (A) and (B) represents (1) Cys block-EBPP[$G_1A_3F_2$]$_6$-CalM-EBPP[$G_1A_3F_2$]$_6$-Cys block, (2) Cys block-EBPP[$G_1A_3F_2$]$_{12}$-CalM-EBPP[$G_1A_3F_2$]$_{12}$-Cys block, (3) Cys block-EBPP[$G_1A_3F_2$]$_{18}$-CalM-EBPP[$G_1A_3F_2$]$_{18}$-Cys block, (4) Cys block-EBPP[$G_1A_3F_2$]$_{24}$-CalM-EBPP[$G_1A_3F_2$]$_{24}$-Cys block, (5) Cys block-EBPP[$G_1A_3F_2$]$_{30}$-CalM-EBPP[$G_1A_3F_2$]$_{30}$-Cys block, and (6) Cys block-EBPP[$G_1A_3F_2$]$_{36}$-CalM-EBPP[$G_1A_3F_2$]$_{36}$-Cys block.

FIG. 7 shows the thermal transition behaviors of the polypeptides in the absence (A) or presence (B) of 10 mM $CaCl_2$ when the polypeptides were characterized by turbidity profiling as a function of temperature at a heating rate of 1° C./min. Depending on different $EBPP[G_1A_3F_2]$ block sizes as a hydrophobic block and calcium binding to the CalM, $T_t$s of the polypeptides were finely controlled in the range from 29.4 to 47.3° C. As the $EBPP[G_1A_3F_2]$ block length increased, the $T_t$ of the polypeptides became lower irrespective of calcium binding to the CalM. In particular, when calcium ions were bound to the CalM, the CalM of the triblock polypeptides underwent a large conformational change, forming a dumbbell shaped structure. Therefore, the $T_t$ of the polypeptides in the presence of 10 mM $CaCl_2$ were approximately 1.6 to 6.2° C. lower than those in the absence of calcium ions due to increased hydrophobicity induced by a large conformational change of the CalM. Potentially, the calcium bound CalM structure in the dumbbell shaped structure at both ends of a long central helix may make the distance between $EBPP[G_1A_3F_2]$ blocks within the triblock polypeptides much shorter than that without calcium.

Example 9: Viscoelastic Behavior of EBP-CalM-EBP Triblock Polypeptides

Figure 8:
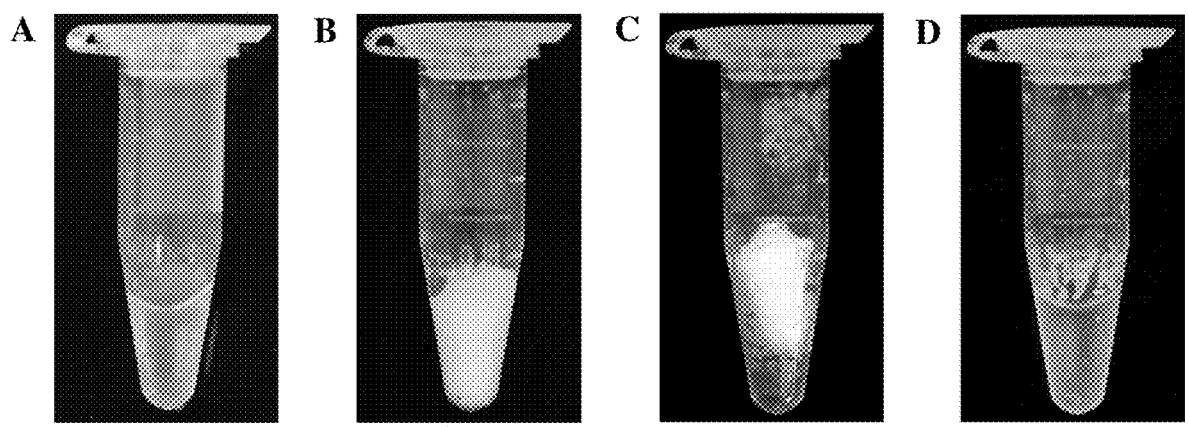
FIG. 8 shows the images of the reversible sol-gel transition behaviors of Cys block-EBPP[$G_1A_3F_2$]$_{12}$-CalM-EBPP[$G_1A_3F_2$]$_{12}$-Cys block in 10 mM HEPES buffer at pH 7.4, as a function of temperature, when sequentially incubated at 4° C. (A), 37° C. (B and C), and 4° C. (D)

FIG. 8 shows photographic images of reversible sol-gel transition behavior of the Cys block-$EBPP[G_1A_3F_2]_{12}$-CalM-$EBPP[G_1A_3F_2]_{12}$-Cys block in 10 mM HEPES buffer at pH 7.4 as a function of temperature. When the EBP-CalM-EBP triblock polypeptide was prepared in HEPES buffer at 27 wt. %, a viscoelastic liquid with viscous flow at 4° C. became a viscoelastic solid at 37° C. due to physical crosslinking between aggregated EBPP blocks within the triblock polypeptide at 37° C. In particular, as shown in FIG. 8(C), the physically cross-linked hydrogel at 37° C. was easily detached from a tube by simply tapping a finger, indicating rheological and mechanical properties of the physically cross-linked hydrogel at 37° C. FIGS. 8(A) to 8(D) show that transition behavior from the viscoelastic solid to the viscoelastic liquid was reversible as temperature decreased from at 37 to 4° C. because of reversible phase transition behavior of an EBPP block as shown in FIGS. 8(A) to 8(D).

Figure 9:
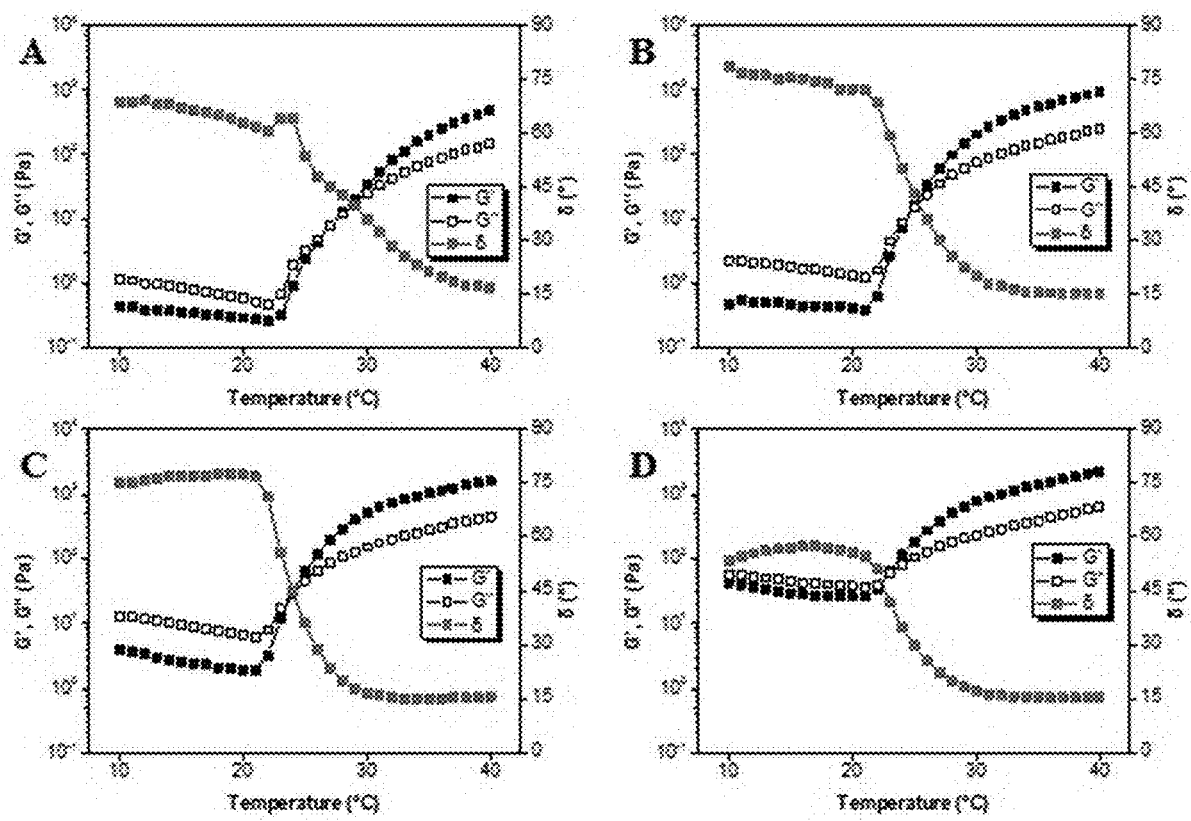
FIG. 9 shows temperature-dependent rheological behaviors of Cys block-EBPP[$G_1A_3F_2$]$_{12}$-CalM-EBPP[$G_1A_3F_2$]$_{12}$-Cys block in 10 mM HEPES buffer at pH 7.4 as a function of polypeptide concentration (1 rad/s, 2% shear strain): (A) 16.6 wt. %, (B) 23.1 wt. %, (C) 27.0 wt. %, and (D) 28.6 wt. %. Storage modulus (G'), loss modulus (G"), and loss angle (δ) obtained by measuring each oscillatory shear were plotted as a function of temperature at a heating rate of 1° C./min.
Figure 10:
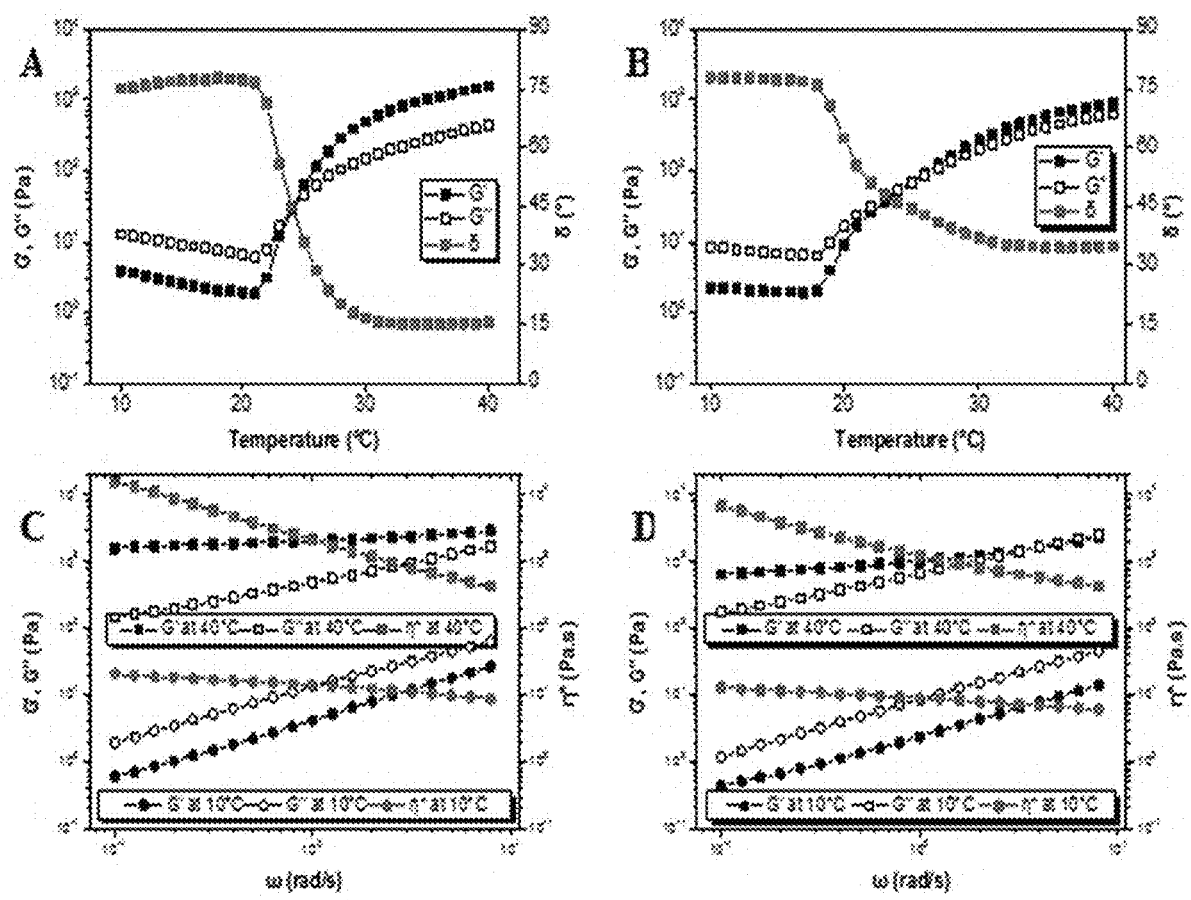
FIG. 10 shows oscillatory rheological profiles of 27.0 wt. % Cys block-EBPP[$G_1A_3F_2$]$_{12}$-CalM-EBPP[$G_1A_3F_2$]$_{12}$-Cys block in 10 mM HEPES buffer (A and C) or in 10 mM HEPES buffer containing 168 mM $CaCl_2$ (B and D), wherein A and B are profiles as a function of temperature at 1 rad/s and 2% shear strain, and C and D are profiles as a function of frequency at 10 or 40° C. and 2% shear strain.

FIGS. 9 and 10 show the temperature and ligand-dependent rheological and mechanical properties of the Cys block-$EBPP[G_1A_3F_2]_{12}$-CalM-$EBPP[G_1A_3F_2]_{12}$-Cys block in 10 mM HEPES buffer at pH 7.4 as functions of polypeptide concentration and $CaCl_2$. A series of independent strain sweep tests were performed in the range from 0.2 to 20% at various angular frequencies of 0.1, 1.0 or 10.0 rad/s. Dynamic frequency sweep measurements at 2% strain were performed in the linear viscoelastic regime at different temperatures. The angular frequency ranged from 0.1 to 10 rad/s, both at 10° C. below $T_t$ and 40° C. above $T_t$ for the dynamic frequency sweep tests. The temperature sweep tests were executed with 2% strain at 1.0 rad/s over a temperature range of 10 to 40° C. with one minute in duration per degree for forward heating and reverse cooling measurements to examine the reversibility of rheological and mechanical properties thereof. The storage modulus (G'), the loss modulus (G"), the complex shear modulus (G*), the complex viscosity ($\eta^*$), and the loss angle ($\delta$) were obtained from each oscillatory shear measurement. FIG. 9 clearly shows controlled gelation temperature (t), which is defined as a temperature of the crossover point of G' and G" in the temperature sweep measurement. As shown in FIG. 9, thermally induced phase transition of the triblock polypeptide in 10 mM HEPES buffer at pH 7.4 occurred at 22 to 23° C. in the concentration range of 16.6-28.6 wt. % and the G' and G" values continued to increase due to intra- or intermolecular hydrophobic interactions between the aggregated EBPP blocks within the triblock polypeptide as the temperature increased. In particular, as the temperature increased above the $T_t$, the complex shear modulus (G*) values largely increased about 3 orders of magnitude greater than that 10° C. below the $T_t$, indicating enhanced stiffness due to the evolved viscoelasticity.

As shown in FIG. 10, an effect of calcium binding to CalM on both thermally induced phase transition and rheological properties of the triblock polypeptide was also characterized by oscillatory rheological measurements when 10 mM HEPES buffer at pH 7.4 was supplemented with 168 mM $CaCl_2$ to have a 10-fold molar excess of $CaCl_2$ as compared to the 4.2 mM EF-hand motif of CalM. Thermally induced phase transition of the triblock polypeptide in the presence of calcium (FIG. 10 (B)) occurred at 19° C., which is 3° C. lower than that without calcium (FIG. 10 (A)) because the CalM of the triblock polypeptides underwent a large conformational change, forming into a dumbbell shaped structure when calcium ions were bound to the CalM. Although the complex shear modulus (G*) showed similar values irrespective of calcium binding to CalM, the loss angle ($\delta$) in the presence of calcium was 36°, which was 20° higher than that without calcium. Potentially, when a large conformational change of CalM of the triblock polypeptides was induced by calcium binding, the calcium bound CalM structure in the dumbbell shaped structure at both ends of a long central helix may make the distance between EBPP[$G_1A_3F_2$] blocks within the triblock polypeptides much shorter than that without calcium, suggesting a lowered viscoelastic solid property. FIGS. 10(C) and 10(D) show the frequency-dependent rheological behavior of the triblock polypeptide without (C) and with (D) calcium binding to CalM at 10 and 40° C. In general, the elastic property at 40° C. dominated over a wide frequency range of 0.1 to 10 rad/s at 2% strain and the values of the complex viscosity (1*) are highly frequency dependent with a 10-fold difference or greater due to a intermolecular physical cross-linking of the aggregated EBPP blocks. This proved that the triblock polypeptide was a physically cross-linked hydrogel in conditions higher than the transition temperature of hydrophobic EBP, and depending on the presence or absence of calcium binding to the CalM, (C) and (D) showed different values of G', G" and $\eta^*$ depending on frequency. These indicated that rheologically and mechanically different protein hydrogels were formed.

TABLE 4

Transition temperature of EBP-CalM-EBP triblock polypeptides in the presence of 10 mM $CaCl_2$ as compared to free calM without $CaCl_2$.

| | EBP-CalM-EBP library | Free CalM (° C.) | CalM with $Ca^{2+}$ (° C.) |
|---|---|---|---|
| A | Cys-EBPP[$G_1A_3F_2$]$_6$-CalM-EBPP[$G_1A_3F_2$]$_6$-Cys | 47.3 | 40.1 |
| B | Cys-EBPP[$G_1A_3F_2$]$_{12}$-CalM-EBPP[$G_1A_3F_2$]$_{12}$-Cys | 43.2 | 36.1 |
| C | Cys-EBPP[$G_1A_3F_2$]$_{18}$-CalM-EBPP[$G_1A_3F_2$]$_{18}$-Cys | 37.4 | 33.5 |
| D | Cys-EBPP[$G_1A_3F_2$]$_{24}$-CalM-EBPP[$G_1A_3F_2$]$_{24}$-Cys | 35.0 | 31.9 |
| E | Cys-EBPP[$G_1A_3F_2$]$_{30}$-CalM-EBPP[$G_1A_3F_2$]$_{30}$-Cys | 32.4 | 30.8 |
| F | Cys-EBPP[$G_1A_3F_2$]$_{36}$-CalM-EBPP[$G_1A_3F_2$]$_{36}$-Cys | 29.4 | 30.7 |

Transition temperature of EBP-CalM-EBP triblock polypeptides in the presence of 10 mM $CaCl_2$ as compared to free CalM without $CaCl_2$.

TABLE 5

Thermal transition temperature (Tt), gelation temperature ($\tau$), complex shear modulus (|G*|) and phase angle ($\delta$) of 27.0 wt. % Cys block-EBPP[$G_1A_3F_2$]$_{12}$-CalM-EBPP[$G_1A_3F_2$]$_{12}$-Cys block in HEPES and HEPES supplemented with 168 mM $CaCl_2$ measured by oscillatory rheological profiles at 1 rad/s and 2% shear strain.

| Solvent | $T_t$ (° C.) | $\tau$ (° C.) | |G*| (Pa) | $\delta$ (°) |
|---|---|---|---|---|
| HEPES | 20.9 | 24.1 | 756.2 | 15.3 |
| HEPES with 168 mM $CaCl_2$ | 17.4 | 24.0 | 404.7 | 33.8 |

The EBP-CalM-EBP triblock polypeptide as an ABA-type showed multi-responsiveness to temperature, calcium and ligand molecules at a molecular level. The physically crosslinked hydrogel of the EBP-CalM-EBP triblock polypeptide was formed by thermal and ligand stimuli, and was found to have reversible sol-gel transition behavior. These dynamic hydrogels also showed different rheological and mechanical properties via multi-responsiveness to calcium, and ligand molecules.

Potentially, the physically crosslinked hydrogels may be further chemically crosslinked via disulfide bonds of the Cys blocks via oxidation, and dityrosine of CalM via light. These multi-responsive dynamic protein hydrogels may be used in drug delivery system, tissue engineering, and regenerative medicine.

The hydrogel according to the present invention can be used in injectable drug delivery systems, functional tissue engineering and regenerative medicine.

What is claimed is:

1. A triblock polypeptide having multi-stimuli responsiveness, wherein the triblock polypeptide is consisted of
   a calmodulin block; and
   polypeptide blocks having a phase transition behavior linked to both ends of the calmodulin block, and is represented by Formula 3 below:

[hydrophobic EBP]m-CalM-[hydrophobic EBP]m, wherein           Formula 3 the [hydrophobic EBP]m refers to a polypeptide block having a phase transition behavior; and the hydrophobic EBP is a pentapeptide of Val-Pro-Ala-Xaa-Gly (SEQ ID NO: 2), wherein Xaa is an amino acid other than proline;
   m is an integer of 2 or more, and is the number of repeats of the hydrophobic polypeptide having a phase transition behavior; and
   the CalM is a calmodulin block, wherein an amino acid sequence encoding the calmodulin is SEQ ID NO: 38.

2. The triblock polypeptide according to claim 1, wherein the [hydrophobic EBP]m, m is multiple of six, and
   the [hydrophobic EBP] is consisted of an amino acid sequence below:
   Val-Pro-Ala-Xaa-Gly [SEQ ID NO: 40], wherein each Xaa of the pentapeptide repeats is consisted of G (Gly), A (Ala), and F (Phe) in a ratio of 1:3:2.

3. The triblock polypeptide according to claim 2, wherein m is 6, 12, 18, 24, 30 or 36.

4. A hydrogel, wherein the hydrogel is prepared by a process comprising:
   applying a heat stimulus to the triblock polypeptide according to claim 1; and
   cross-linking hydrophobic EBPs of the triblock polypeptide by the heat stimulus and forming a hydrogel.

5. The hydrogel according to claim 4, wherein the hydrogel is prepared by a process comprising:
   after the hydrophobic EBPs are cross-linked,
   inducing a structural change of the calmodulin by specifically binding the calmodulin block, which constitutes the triblock polypeptide, to a ligand; and
   forming a dynamic hydrogel by a three-dimensional structural change of the hydrogel induced by the structural change of the calmodulin block due to the ligand responsiveness.

6. The hydrogel according to claim 4, wherein, in the cross-linking, the cross-linking is physical cross-linking that occurs at or above a transition temperature of the hydrophobic EBP.

7. The hydrogel according to claim 5, wherein the ligand is calcium and/or a drug.

8. The hydrogel according to claim 4, wherein the hydrogel is formed by dityrosine cross-linking, which is generated by chemically cross-linking tyrosine residues within a calmodulin block constituting the triblock peptide.

9. A composition for drug delivery comprising the hydrogel according to claim 4.

10. A scaffold for tissue engineering comprising the hydrogel according to claim 4.

11. A kit for tissue or organ regeneration comprising the hydrogel according to claim 4.

\* \* \* \* \*

SEQUENCE LISTING

<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<223> OTHER INFORMATION: Elastin-based peptide (EBP), Xaa can be any

```
       amino acid, natural or non-natural
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Val Pro Gly Xaa Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Elastin-based peptide (EBP), Xaa can be any
      amino acid, natural or non-natural
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2

Val Pro Ala Xaa Gly
1               5

<210> SEQ ID NO 3
<211> LENGTH: 90
<212> TYPE: DNA
<213> ORGANISM: Artificial Sequence
<220> FEATURE:
<223> OTHER INFORMATION: EBP

<400> SEQUENCE: 3
gtcccaggtg gaggtgtacc cggcgcgggt gtcccaggtg gaggtgtacc tgggggtggg      60
gtccctggta ttggcgtacc tggaggcggc                                      90

<210> SEQ ID NO 4
<211> LENGTH: 90
<212> TYPE: DNA
<213> ORGANISM: Artificial Sequence
<220> FEATURE:
<223> OTHER INFORMATION: EBP

<400> SEQUENCE: 4
gttccagctg gcggtgtacc tgctgctgct gttccggccg gtggtgttcc ggcgggcggc      60
gtgcctgcaa taggagttcc cgctggtggc                                      90

<210> SEQ ID NO 5
<211> LENGTH: 90
<212> TYPE: DNA
<213> ORGANISM: Artificial Sequence
<220> FEATURE:
<223> OTHER INFORMATION: EBP

<400> SEQUENCE: 5
gttccgggtg gtggtgttcc gggtaaaggt gttccgggtg gtggtgttcc gggtggtggt      60
ggtgttccgg gtatcggtgt tccgggtggc                                      90

<210> SEQ ID NO 6
<211> LENGTH: 90
<212> TYPE: DNA
<213> ORGANISM: Artificial Sequence
<220> FEATURE:
<223> OTHER INFORMATION: EBP
```

-continued

<400> SEQUENCE: 6
gttccggcgg gtggtgttcc ggcgaaaggt gttccggcgg gtggtgttcc ggcgggtggt    60
gttccggcga tcggtgttcc ggcgggtggc    90

<210> SEQ ID NO 7
<211> LENGTH: 90
<212> TYPE: DNA
<213> ORGANISM: Artificial Sequence
<220> FEATURE:
<223> OTHER INFORMATION: EBP

<400> SEQUENCE: 7
gttccgggtg gtggtgttcc gggtgatggt gttccgggtg gtggtgttcc gggtggtggt    60
ggtgttccgg gtatcggtgt tccgggtggc    90

<210> SEQ ID NO 8
<211> LENGTH: 90
<212> TYPE: DNA
<213> ORGANISM: Artificial Sequence
<220> FEATURE:
<223> OTHER INFORMATION: EBP

<400> SEQUENCE: 8
gttccggcgg gtggtgttcc ggcggatggt gttccggcgg gtggtgttcc ggcgggtggt    60
gttccggcga tcggtgttcc ggcgggtggc    90

<210> SEQ ID NO 9
<211> LENGTH: 90
<212> TYPE: DNA
<213> ORGANISM: Artificial Sequence
<220> FEATURE:
<223> OTHER INFORMATION: EBP

<400> SEQUENCE: 9
gttccgggtg gtggtgttcc gggtgaaggt gttccgggtg gtggtgttcc gggtggtggt    60
ggtgttccgg gtatcggtgt tccgggtggc    90

<210> SEQ ID NO 10
<211> LENGTH: 90
<212> TYPE: DNA
<213> ORGANISM: Artificial Sequence
<220> FEATURE:
<223> OTHER INFORMATION: EBP

<400> SEQUENCE: 10
gttccggcgg gtggtgttcc ggcggaaggt gttccggcgg gtggtgttcc ggcgggtggt    60
gttccggcga tcggtgttcc ggcgggtggc    90

<210> SEQ ID NO 11
<211> LENGTH: 90
<212> TYPE: DNA
<213> ORGANISM: Artificial Sequence
<220> FEATURE:
<223> OTHER INFORMATION: EBP

<400> SEQUENCE: 11
gtcccgggtg cgggcgtgcc gggatttgga gttccgggtg cgggtgttcc aggcggtggt    60
gttccgggcg cgggcgtgcc gggctttggc    90

<210> SEQ ID NO 12
<211> LENGTH: 90

<212> TYPE: DNA
<213> ORGANISM: Artificial Sequence
<220> FEATURE:
<223> OTHER INFORMATION: EBP

<400> SEQUENCE: 12
gtgccggcgg cgggcgttcc agcctttggt gtgccagcgg cgggagttcc ggccggtggc    60
gtgccggcag cgggcgtgcc ggcttttggc    90

<210> SEQ ID NO 13
<211> LENGTH: 90
<212> TYPE: DNA
<213> ORGANISM: Artificial Sequence
<220> FEATURE:
<223> OTHER INFORMATION: EBP

<400> SEQUENCE: 13
gtgccggcgg cgggcgttcc agcctttggt gtgccagcgg cgggagttcc ggccaaaggc    60
gtgccggcag cgggcgtgcc ggcttttggc    90

<210> SEQ ID NO 14
<211> LENGTH: 90
<212> TYPE: DNA
<213> ORGANISM: Artificial Sequence
<220> FEATURE:
<223> OTHER INFORMATION: EBP

<400> SEQUENCE: 14
gtgccggcgg cgggcgttcc agcctttggt gtgccagcgg cgggagttcc ggccgatggc    60
gtgccggcag cgggcgtgcc ggcttttggc    90

<210> SEQ ID NO 15
<211> LENGTH: 90
<212> TYPE: DNA
<213> ORGANISM: Artificial Sequence
<220> FEATURE:
<223> OTHER INFORMATION: EBP

<400> SEQUENCE: 15
gttccagcgt ttggcgtgcc agcgaaaggt gttccggcgt ttggggttcc cgcgaaaggt    60
gtgccggcct ttggtgtgcc ggccaaaggc    90

<210> SEQ ID NO 16
<211> LENGTH: 90
<212> TYPE: DNA
<213> ORGANISM: Artificial Sequence
<220> FEATURE:
<223> OTHER INFORMATION: EBP

<400> SEQUENCE: 16
gttccagcgt ttggcgtgcc agcggatggt gttccggcgt ttggggttcc cgcggatggt    60
gtgccggcct ttggtgtgcc ggccgatggc    90

<210> SEQ ID NO 17
<211> LENGTH: 90
<212> TYPE: DNA
<213> ORGANISM: Artificial Sequence
<220> FEATURE:
<223> OTHER INFORMATION: EBP

<400> SEQUENCE: 17
gtgccggcgc atggagttcc tgccgccggt gttcctgcgc atggtgtacc ggcaattggc    60

```
gttccggcac atggtgtgcc ggccgccggc                                           90
```

<210> SEQ ID NO 18
<211> LENGTH: 90
<212> TYPE: DNA
<213> ORGANISM: Artificial Sequence
<220> FEATURE:
<223> OTHER INFORMATION: EBP

<400> SEQUENCE: 18

```
gttccggccg gaggtgtacc ggcgcatggt gttccggcac atggtgtgcc ggctcacggt         60
gtgcctgcgc atggcgttcc tgcgcatggc                                           90
```

<210> SEQ ID NO 19
<211> LENGTH: 90
<212> TYPE: DNA
<213> ORGANISM: Artificial Sequence
<220> FEATURE:
<223> OTHER INFORMATION: EBP

<400> SEQUENCE: 19

```
gtgccggcgt gcggcgttcc agcctttggt gtgccagcgt gcggagttcc ggccggtggc         60
gtgccggcat gcggcgtgcc ggcttttggc                                           90
```

<210> SEQ ID NO 20
<211> LENGTH: 30
<212> TYPE: PRT
<213> ORGANISM: Artificial Sequence
<220> FEATURE:
<223> OTHER INFORMATION: EBP

<400> SEQUENCE: 20

Val Pro Gly Gly Gly Val Pro Gly Ala Gly Val Pro Gly Gly Gly Val
1               5                   10                  15
Pro Gly Gly Gly Val Pro Gly Ile Gly Val Pro Gly Gly Gly
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: EBP

<400> SEQUENCE: 21

Val Pro Ala Gly Gly Val Pro Ala Ala Gly Val Pro Ala Gly Gly Val
1               5                   10                  15
Pro Ala Gly Gly Val Pro Ala Ile Gly Val Pro Ala Gly Gly
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: EBP

<400> SEQUENCE: 22

Val Pro Gly Gly Gly Val Pro Gly Lys Gly Val Pro Gly Gly Gly Val
1               5                   10                  15
Pro Gly Gly Gly Val Pro Gly Ile Gly Val Pro Gly Gly Gly
            20                  25                  30

-continued

```
<210> SEQ ID NO 23
<211> LENGTH: 30
<212> TYPE: PRT
<213> ORGANISM: Artificial Sequence
<220> FEATURE:
<223> OTHER INFORMATION: EBP

<400> SEQUENCE: 23

Val Pro Ala Gly Gly Val Pro Ala Lys Gly Val Pro Ala Gly Gly Val
1               5                   10                  15
Pro Ala Gly Gly Val Pro Ala Ile Gly Val Pro Ala Gly Gly
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: EBP

<400> SEQUENCE: 24

Val Pro Gly Gly Gly Val Pro Gly Asp Gly Val Pro Gly Gly Gly Val
1               5                   10                  15
Pro Gly Gly Gly Val Pro Gly Ile Gly Val Pro Gly Gly Gly
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: EBP

<400> SEQUENCE: 25

Val Pro Ala Gly Gly Val Pro Ala Asp Gly Val Pro Ala Gly Gly Val
1               5                   10                  15
Pro Ala Gly Gly Val Pro Ala Ile Gly Val Pro Ala Gly Gly
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: EBP

<400> SEQUENCE: 26

Val Pro Gly Gly Gly Val Pro Gly Glu Gly Val Pro Gly Gly Gly Val
1               5                   10                  15
Pro Gly Gly Gly Val Pro Gly Ile Gly Val Pro Gly Gly Gly
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: EBP

<400> SEQUENCE: 27

Val Pro Ala Gly Gly Val Pro Ala Glu Gly Val Pro Ala Gly Gly Val
1               5                   10                  15
Pro Ala Gly Gly Val Pro Ala Ile Gly Val Pro Ala Gly Gly
            20                  25                  30
```

```
<210> SEQ ID NO 28
<211> LENGTH: 30
<212> TYPE: PRT
<213> ORGANISM: Artificial Sequence
<220> FEATURE:
<223> OTHER INFORMATION: EBP

<400> SEQUENCE: 28

Val Pro Gly Ala Gly Val Pro Gly Phe Gly Val Pro Gly Ala Gly Val
1               5                   10                  15

Pro Gly Gly Gly Val Pro Gly Ala Gly Val Pro Gly Phe Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: EBP

<400> SEQUENCE: 29

Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: EBP

<400> SEQUENCE: 30

Val Pro Ala Ala Gly Val Pro Ala Phe Gly Val Pro Ala Ala Gly Val
1               5                   10                  15

Pro Ala Lys Gly Val Pro Ala Ala Gly Val Pro Ala Phe Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: EBP

<400> SEQUENCE: 31

Val Pro Ala Ala Gly Val Pro Ala Phe Gly Val Pro Ala Ala Gly Val
1               5                   10                  15

Pro Ala Asp Gly Val Pro Ala Ala Gly Val Pro Ala Phe Gly
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: EBP

<400> SEQUENCE: 32

Val Pro Ala Phe Gly Val Pro Ala Lys Gly Val Pro Ala Phe Gly Val
1               5                   10                  15

Pro Ala Lys Gly Val Pro Ala Phe Gly Val Pro Ala Lys Gly
            20                  25                  30
```

<210> SEQ ID NO 33
<211> LENGTH: 30
<212> TYPE: PRT
<213> ORGANISM: Artificial Sequence
<220> FEATURE:
<223> OTHER INFORMATION: EBP

<400> SEQUENCE: 33

Val Pro Ala Phe Gly Val Pro Ala Asp Gly Val Pro Ala Phe Gly Val
1               5                   10                  15

Pro Ala Asp Gly Val Pro Ala Phe Gly Val Pro Ala Asp Gly
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: EBP

<400> SEQUENCE: 34

Val Pro Ala His Gly Val Pro Ala Ala Gly Val Pro Ala His Gly Val
1               5                   10                  15

Pro Ala Ile Gly Val Pro Ala His Gly Val Pro Ala Ala Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: EBP

<400> SEQUENCE: 35

Val Pro Ala Gly Gly Val Pro Ala His Gly Val Pro Ala His Gly Val
1               5                   10                  15

Pro Ala His Gly Val Pro Ala His Gly Val Pro Ala His Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: EBP

<400> SEQUENCE: 36

Val Pro Ala Cys Gly Val Pro Ala Phe Gly Val Pro Ala Cys Gly Val
1               5                   10                  15

Pro Ala Gly Gly Val Pro Ala Cys Gly Val Pro Ala Phe Gly
            20                  25                  30

<210> SEQ ID NO 37
<211> LENGTH: 438
<212> TYPE: DNA
<213> ORGANISM: Rattus norvegicus

<400> SEQUENCE: 37
gctgaccagc tgaccgaaga acagattgca gagttcaagg aagccttctc cctctttgac    60
aaggatggag atggcaccat taccaccaag gagctgggga ctgtgatgag atcgctgggg   120
caaaacccca ctgaggcgga actgcaggac atgatcaatg aggtggatgc tgatggcaat   180

```
gggaccattg acttcccaga gttcctgacc atgatggcca gaaagatgaa ggatacagac    240
agcgaggaag agataccaga ggccttccgt gtctttgaca aggatgggaa tggctacatc    300
agtgctgctg agctgcgtca cgtcatgacg aacctggggg agaagctgac tgatgaggaa    360
gtggatgaga tgatccgaga ggcggacatt gatggaggcg gccaggtcaa ttatgaagag    420
tttgtacaga tgatgact                                                  438
```

<210> SEQ ID NO 38
<211> LENGTH: 146
<212> TYPE: PRT
<213> ORGANISM: Rattus norvegicus

<400> SEQUENCE: 38

```
Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Pro Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Gly Gly Gln Val Asn Tyr Glu Glu Phe Val Gln Met
    130                 135                 140

Met Thr
145
```

<210> SEQ ID NO 39
<211> LENGTH: 12
<212> TYPE: PRT
<213> ORGANISM: Artificial Sequence
<220> FEATURE:
<223> OTHER INFORMATION: Cys block

<400> SEQUENCE: 39

```
Gly Ala Cys Gly Ala Cys Gly Ala Cys Gly Ala Cys
1               5                   10
```

<210> SEQ ID NO 40
<211> LENGTH: 30
<212> TYPE: PRT
<213> ORGANISM: Artificial Sequence
<220> FEATURE:
<223> OTHER INFORMATION: EBP
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)

```
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 40

Val Pro Ala Xaa Gly Val Pro Ala Xaa Gly Val Pro Ala Xaa Gly Val
1               5                   10                  15

Pro Ala Xaa Gly Val Pro Ala Xaa Gly Val Pro Ala Xaa Gly
            20                  25                  30

<210> SEQ ID NO 41
<211> LENGTH: 66
<212> TYPE: DNA
<213> ORGANISM: Artificial Sequence
<220> FEATURE:
<223> OTHER INFORMATION: EBP

<400> SEQUENCE: 41
ctagaaataa ttttgtttaa ctttaagaag gaggagtaca tatgggctac tgataatgat    60
cttcag                                                               66

<210> SEQ ID NO 42
<211> LENGTH: 66
<212> TYPE: DNA
<213> ORGANISM: Artificial Sequence
<220> FEATURE:
<223> OTHER INFORMATION: EBP

<400> SEQUENCE: 42
gatcctgaag atcattatca gtagcccata tgtactcctc cttcttaaag ttaaacaaaa    60
ttattt                                                               66

<210> SEQ ID NO 43
<211> LENGTH: 5
<212> TYPE: PRT
<213> ORGANISM: Artificial Sequence
<220> FEATURE:
<223> OTHER INFORMATION: Elastin-based peptide
<220> FEATURE:
<221> NAME/KEY: misc_feature
<222> LOCATION: (3)..(3)
<223> OTHER INFORMATION: Xaa can be Gly or Ala
<220> FEATURE:
<221> NAME/KEY: misc_feature
<222> LOCATION: (4)..(4)
<223> OTHER INFORMATION: Xaa can be any naturally occurring amino acid

<400> SEQUENCE: 43

Val Pro Xaa Xaa Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Elastin-based peptide
```

```
<400> SEQUENCE: 44

Val Pro Gly Val Gly
1               5

<210> SEQ ID NO 45
<211> LENGTH: 30
<212> TYPE: PRT
<213> ORGANISM: Artificial Sequence
<220> FEATURE:
<223> OTHER INFORMATION: EBP
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 45

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly
            20                  25                  30
```